(12) United States Patent
Kimura

(10) Patent No.: US 6,780,529 B2
(45) Date of Patent: Aug. 24, 2004

(54) HETEROCYCLIC COMPOUND AND LIGHT-EMITTING DEVICE USING SAME

(75) Inventor: Keizo Kimura, Kanagawa-ken (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 10/097,607

(22) Filed: Mar. 15, 2002

(65) Prior Publication Data

US 2003/0072965 A1 Apr. 17, 2003

(30) Foreign Application Priority Data

Mar. 16, 2001 (JP) ........................................ 2001-076704
Oct. 23, 2001 (JP) ........................................ 2001-325594

(51) Int. Cl.$^7$ ........................ H05B 33/14; C07D 473/00

(52) U.S. Cl. ........................ 428/690; 428/917; 313/504; 257/102; 257/103; 252/301.16; 544/264

(58) Field of Search ................................ 428/690, 917; 313/504, 506; 257/102, 103; 252/301.16; 544/264

(56) References Cited

U.S. PATENT DOCUMENTS 6,461,747 B1 * 10/2002 Okada et al. ............... 428/690

* cited by examiner

Primary Examiner—Marie Yamnitzky
(74) Attorney, Agent, or Firm—Sughrue Mion, PLLC

(57) ABSTRACT

A light-emitting device comprising a pair of electrodes and one or more organic layers disposed therebetween, the one or more organic layers comprising a light-emitting layer, wherein at least one of the one or more organic layers comprises a compound represented by the following formula (I):

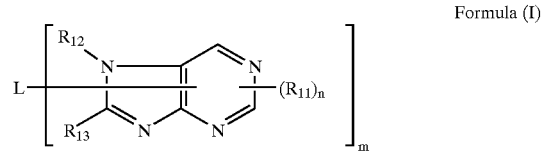

Formula (I)

wherein $R_{11}$ represents a substituent; $R_{12}$ represents a hydrogen atom, an aliphatic hydrocarbon group, an aryl group or a heterocyclic group; $R_{13}$ represents a hydrogen atom or a substituent; n represents an integer of 0 to 2; L represents a single bond or a linking group; and m represents an integer of 2 or more.

9 Claims, No Drawings

HETEROCYCLIC COMPOUND AND LIGHT-EMITTING DEVICE USING SAME

FIELD OF THE INVENTION

The present invention relates to a light-emitting device that converts electric energy into light to be useful for indicating elements, display devices, backlights, electrophotographies, illumination light sources, recording light sources, exposing light sources, reading light sources, road signs and markings, signboards, interiors, optical communications, etc. The present invention further relates to a heterocyclic compound usable for the light-emitting device, especially for an organic electroluminescence device.

BACKGROUND OF THE INVENTION

Recently, various display devices have been widely studied. In particular, organic electroluminescence (EL) devices are advantageous in that they can emit light with high luminance by a lowered applying voltage, whereby much attention has been paid thereto. For example, a light-emitting device comprising organic thin layers provided by vapor-depositing organic compounds has been disclosed in Applied Physics Letters, 51, 913 (1987). This light-emitting device has a structure where an electron-transporting material of tris(8-hydroxyquinolinato) aluminum complex (Alq) and a hole-transporting material of an amine compound are disposed between electrodes as a laminate, thereby exhibiting more excellent light-emitting properties than that of conventional light-emitting devices having a single-layer structure.

The above light-emitting device having the laminate structure can be improved with respect to light-emitting efficiency by doping the device with a fluorescent compound such as a coumarin dye, etc. as disclosed in Journal of Applied Physics, Vol.65, Page 3610, 1989, etc. Emission wavelength can be controlled by changing the fluorescent compound. However, in the case of using Alq as a charge-transporting material for the light-emitting device, particularly for a blue light-emitting device, green light emission due to Alq is observed in addition to light emission by the doped fluorescent compound when the driving voltage is increased to obtain high luminance. As a result, the light-emitting device is reduced in the color purity. Therefore, it has been desired to develop a host material that can suppress the reduction of the color purity, and for example, Japanese Patent Laid-Open No. 10-92578 and U.S. Pat. No. 5,766,779 have disclosed that a particular indole derivative can be used as the host material to provide a blue light-emitting device high in the color purity. However, the device using the indole derivative needs high driving voltage to obtain a high luminance, and thus it has been desirable to develop a material, a light-emitting device using the same providing high luminance with low driving voltage.

Further, though it is known that the light-emitting efficiency of the light-emitting device can be improved by a method using a hole-blocking material such as 3-(biphenyl-4-yl)-4-phenyl-5-(4-tert-butylphenyl)-1,2,4-triazole (TAZ), bathocuproine (BCP), etc., the device using the hole-blocking material is poor in durability. In particular, such light-emitting device is disadvantageous in that the properties of the device are worsened during high temperature storage or continuous operation.

Among the conventional light-emitting devices, such that comprises a charge-transporting material doped with a small amount of a fluorescent compound is excellent in the color purity and the light-emitting efficiency. However, such a light-emitting device is poor in reproducibility of the light emission. Further, the fluorescent compound is low in durability, whereby reduction of the luminance, change of the emission color, etc. is caused when the device is used for a long-term. Proposal has been made to overcome such problems is a method of using a material having both of a charge-transporting property and a light-emitting property. However, in the case of using the fluorescent compound at a high concentration, the device using the material is poor in luminance because of concentration quenching, association of the fluorescent compound, etc.

Although the organic layer of the organic light-emitting device may be formed by a vapor deposition method, a sputtering method, a coating method, etc., the organic layer is desirably formed by the coating method from the viewpoints of simplification of production processes, improvement of workability, application to a flexible device having a large emitting area, etc. However, the organic layer has been generally formed by the vapor deposition method in the conventional organic light-emitting devices high in the luminance, and the light-emitting devices produced by the coating method have been poor in the luminance and the light-emitting efficiency.

OBJECT AND SUMMARY OF THE INVENTION

An object of the present invention is to provide a light-emitting device excellent in light-emitting properties, durability in repeated use and color purity. Another object of the present invention is to provide a heterocyclic compound that is usable for the light-emitting device and has a wide applicability for an electronic device, etc.

As a result of intense research in view of the above objects, the inventor has found that a light-emitting device using a particular compound having a purine skeleton is excellent in light-emitting properties, durability and color purity. The present invention has been accomplished by the finding.

Thus, a light-emitting device of the present invention comprises a pair of electrodes and one or more organic layers disposed between the electrodes, the one or more organic layers comprising a light-emitting layer, wherein at least one of the one or more organic layers comprises a compound having a purine skeleton represented by the following formula (I).

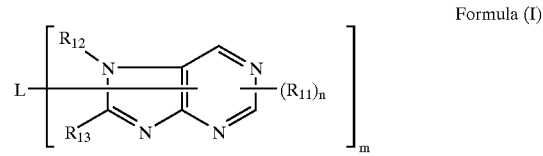

Formula (I)

In the formula (I), $R_{11}$ represents a substituent; $R_{12}$ represents a hydrogen atom, an aliphatic hydrocarbon group, an aryl group or a heterocyclic group; $R_{13}$ represents a hydrogen atom or a substituent; n represents an integer of 0 to 2; L represents a single bond or a linking group; and m represents an integer of 2 or more.

It is preferred that the compound represented by the formula (I) is further represented by any one of the following formulae (II) and (XI).

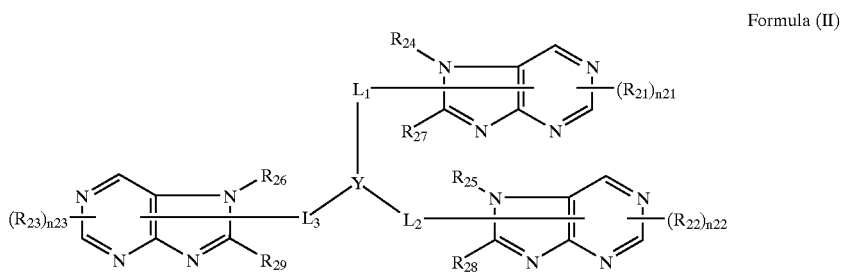

Formula (II)

In the formula (II), $R_{21}$, $R_{22}$ and $R_{23}$ represent a substituent, respectively; $R_{24}$, $R_{25}$ and $R_{26}$ represent a hydrogen atom, an aliphatic hydrocarbon group, an aryl group or a heterocyclic group, respectively; $R_{27}$, $R_{28}$ and $R_{29}$ represent a hydrogen atom or a substituent, respectively; n21, n22 and n23 represent an integer of 0 to 2, respectively; $L_1$, $L_2$ and $L_3$ represent a single bond or a linking group, respectively; and Y represents a nitrogen atom or a 1,3,5-benzenetriyl group.

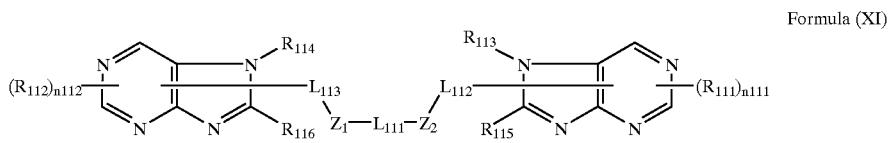

Formula (XI)

In the formula (XI), $R_{111}$ and $R_{112}$ represent a substituent, respectively; $R_{113}$ and $R_{114}$ represent a hydrogen atom, an aliphatic hydrocarbon group, an aryl group or a heterocyclic group, respectively; $R_{115}$ and $R_{116}$ represent a hydrogen atom or a substituent, respectively; n111 and n112 represent an integer of 0 to 2, respectively; $Z_1$ and $Z_2$ represent an arylene group or a divalent aromatic heterocyclic group, respectively; $L_{111}$ represents a single bond or a linking group; and $L_{112}$ and $L_{113}$ represent a single bond, —O—, —S— or —N($R_{117}$)—, respectively, in which $R_{117}$ represents a hydrogen atom, an aliphatic hydrocarbon group, an aryl group or a heterocyclic group.

It is preferred that the compound represented by the formula (II) is furthermore represented by any one of the following formulae (III) and (IV). It is preferred that the compound represented by the formula (XI) is furthermore represented by any one of the following formulae (XII) and (XIII). The heterocyclic compound of the present invention represented by the formula (III), (IV), (XII) or (XIII) has a wide applicability for an electronic device, etc.

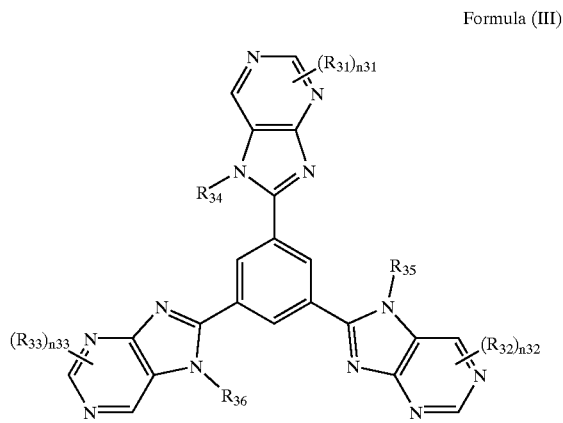

Formula (III)

In the formula (III), $R_{31}$, $R_{32}$ and $R_{33}$ represent a substituent, respectively; $R_{34}$, $R_{35}$ and $R_{36}$ represent a hydrogen atom, an aliphatic hydrocarbon group, an aryl group or a heterocyclic group, respectively; and n31, n32 and n33 represent an integer of 0 to 2, respectively.

Formula (IV)

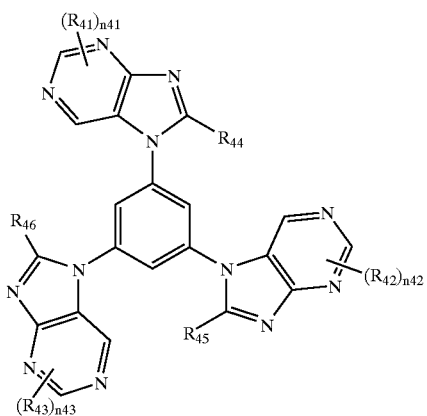

In the formula (IV), $R_{41}$, $R_{42}$ and $R_{43}$ represent a substituent, respectively; $R_{44}$, $R_{45}$ and $R_{46}$ represent a hydrogen atom or a substituent, respectively; and n41, n42 and n43 represent an integer of 0 to 2, respectively.

Formula (XII)

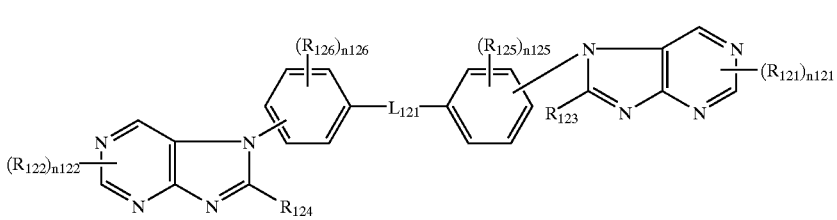

In the formula (XII), $R_{121}$ and $R_{122}$ represent a substituent, respectively; $R_{123}$ and $R_{124}$ represent a hydrogen atom or a substituent, respectively; $R_{125}$ and $R_{126}$ represent a substituent, respectively; n121 and n122 represent an integer of 0 to 2, respectively; n125 and n126 represent an integer of 0 to 4, respectively; and $L_{121}$ represents a single bond or a linking group.

Formula (XIII)

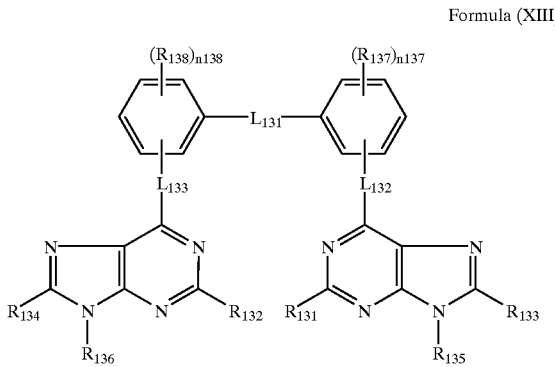

In the formula (XIII), $R_{131}$ and $R_{132}$ represent a hydrogen atom or a substituent, respectively; $R_{133}$ and $R_{134}$ represent a hydrogen atom or a substituent, respectively; $R_{135}$ and $R_{136}$ represent a hydrogen atom, an aliphatic hydrocarbon group, an aryl group or a heterocyclic group, respectively; $R_{137}$ and $R_{138}$ represent a substituent, respectively; n137 and n138 represent an integer of 0 to 4, respectively; $L_{131}$ represents a single bond or a linking group; and $L_{132}$ and $L_{133}$ represent a single bond, —O—, —S— or —N($R_{139}$)—, respectively, in which $R_{139}$ represents a hydrogen atom, an aliphatic hydrocarbon group, an aryl group or a heterocyclic group.

In the organic layer comprising the compound represented by the formula (I), the compound is preferably dispersed in a polymer. Further, it is preferred that the organic layer comprising the compound represented by the formula (I) further comprises a transition metal complex. The transition metal complex is preferably an ortho-metallation complex. Weight ratio of the compound represented by the formula (I) is preferably 1 to 99 weight % based on the total of the organic layer comprising the compound when the compound is used as a host material. Further, the weight ratio is preferably 1 to 100 weight % when the compound is used as a material other than the host material.

Incidentally, although the compound having the purine skeleton according to the present invention falls within claims attached to the specification of Japanese Patent Laid-Open No. 2000-63818, the compound according to the present invention is not recited concretely or specifically in the specification of Japanese Patent Laid-Open No. 2000-63818 so that a structure, superior result and advantage of the subject matter of the present invention have been unexpected by those skilled in the art based on the specification.

DETAILED DESCRIPTION OF THE PREFERRED EMBODIMENTS

[1] Compound Having Purine Skeleton

A light-emitting device of the present invention comprises a compound having a purine skeleton. It is preferred that the compound has a plurality of the purine skeletons, or both of the purine skeleton and another azole skeleton. The compound particularly preferably has a plurality of the purine skeletons. The azole skeleton may be monocyclic or polycyclic, and examples thereof include an imidazole skeleton, a benzimidazole skeleton, a naphthoimidazole skeleton, a thiazole skeleton, a benzthiazole skeleton, a naphthothiazole skeleton, an isothiazole skeleton, an oxazole skeleton, a benzoxazole skeleton, a naphthoxazole skeleton, an isoxazole skeleton, a selenazole skeleton, a benzselenazole skeleton, a naphthoselenazole skeleton, a pyrazole skeleton, an indazole skeleton, a triazole skeleton, a benzotriazole skeleton, a 4-azabenzimidazal skeleton, etc. The azole skeleton is preferably an imidazole skeleton, a benzimidazole skeleton, a naphthoimidazole skeleton, a benzthiazole skeleton, an oxazole skeleton, a benzoxazole skeleton, an isoxazole skeleton, an indazole skeleton, a benzotriazole skeleton or a 4-azabenzimidazal skeleton, more preferably a benzimidazole skeleton, a benzoxazole skeleton, an indazole skeleton or a 4-azabenzimidazal skeleton.

The compound having the purine skeleton is represented by the following formula (I). The compound represented by the formula (I) is hereinafter referred to as "compound (I)".

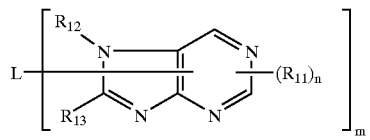

Formula (I)

In the formula (I), $R_{11}$ represents a substituent and examples thereof include: alkyl groups, the number of carbon atom thereof being preferably 1 to 30, more preferably 1 to 20, particularly preferably 1 to 10, such as a methyl group, an ethyl group, an isopropyl group, a t-butyl group, a n-octyl group, a n-decyl group, a n-hexadecyl group, a cyclopropyl group, a cyclopentyl group and a cyclohexyl group; alkenyl groups, the number of carbon atoms thereof being preferably 2 to 30, more preferably 2 to 20, particularly preferably 2 to 10, such as a vinyl group, an allyl group, a 2-butenyl group and a 3-pentenyl group; alkynyl groups, the number of carbon atoms thereof being preferably 2 to 30, more preferably 2 to 20, particularly preferably 2 to 10, such as a propargyl group and a 3-pentynyl group; aryl groups, the number of carbon atoms thereof being preferably 6 to 30, more preferably 6 to 20, particularly preferably 6 to 12, such as a phenyl group, a p-methylphenyl group and a naphtyl group; amino groups, the number of carbon atom thereof being preferably 0 to 30, more preferably 0 to 20, particularly preferably 0 to 10, such as a unsubstituted amino group, a methylamino group, a dimethylamino group, a diethylamino group, a dibenzylamino group, a diphenylamino group and a ditolylamino group; alkoxy groups, the number of carbon atom thereof being preferably 1 to 30, more preferably 1 to 20, particularly preferably 1 to 10, such as a methoxy group, an ethoxy group, a butoxy group and a 2-ethylhexyloxy group; aryloxy groups, the number of carbon atoms thereof being preferably 6 to 30, more preferably 6 to 20, particularly preferably 6 to 12, such as a phenyloxy group, a 1-naphthyloxy group and a 2-naphthyloxy group; acyl groups, the number of carbon atom thereof being preferably 1 to 30, more preferably 1 to 20, particularly preferably 2 to 12, such as an acetyl group, a benzoyl group, a formyl group and a pivaloyl group; alkoxycarbonyl groups, the number of carbon atoms thereof being preferably 2 to 30, more preferably 2 to 20, particularly preferably 2 to 12, such as a methoxycarbonyl group and an ethoxycarbonyl group; aryloxycarbonyl groups, the number of carbon atoms thereof being preferably 7 to 30, more preferably 7 to 20, particularly preferably 7 to 12, such as a phenyloxycarbonyl group; acyloxy groups, the number of carbon atoms thereof being preferably 2 to 30, more preferably 2 to 20, particularly preferably 2 to 10, such as an acetoxy group and a benzoyloxy group; acylamino groups, the number of carbon atoms thereof being preferably 2 to 30, more preferably 2 to 20, particularly preferably 2 to 10, such as an acetylamino group and a benzoylamino group; alkoxycarbonylamino groups, the number of carbon atoms thereof being preferably 2 to 30, more preferably 2 to 20, particularly preferably 2 to 12, such as a methoxycarbonylamino group; aryloxycarbonylamino groups, the number of carbon atoms thereof being preferably 7 to 30, more preferably 7 to 20, particularly preferably 7 to 12, such as a phenyloxycarbonylamino group; sulfonylamino groups, the number of carbon atom thereof being preferably 1 to 30, more preferably 1 to 20, particularly preferably 1 to 12, such as a methane sulfonylamino group and a benzene sulfonylamino group; sulfamoyl groups, the number of carbon atom thereof being preferably 0 to 30, more preferably 0 to 20, particularly preferably 0 to 12, such as a unsubstituted sulfamoyl group, a methylsulfamoyl group, a dimethylsulfamoyl group and a phenylsulfamoyl group; carbamoyl groups, the number of carbon atom thereof being preferably 1 to 30, more preferably 1 to 20, particularly preferably 1 to 12, such as a unsubstituted carbamoyl group, a methylcarbamoyl group, a diethylcarbamoyl group and a phenylcarbamoyl group; alkylthio groups, the number of carbon atom thereof being preferably 1 to 30, more preferably 1 to 20, particularly preferably 1 to 12, such as a methylthio group and an ethylthio group; arylthio groups, the number of carbon atoms thereof being preferably 6 to 30, more preferably 6 to 20, particularly preferably 6 to 12, such as a phenylthio group; sulfonyl groups, the number of carbon atom thereof being preferably 1 to 30, more preferably 1 to 20, particularly preferably 1 to 12, such as a mesyl group and a tosyl group; sulfinyl groups, the number of carbon atom thereof being preferably 1 to 30, more preferably 1 to 20, particularly preferably 1 to 12, such as a methane sulfinyl group and a benzene sulfinyl group; ureide groups, the number of carbon atom thereof being preferably 1 to 30, more preferably 1 to 20, particularly preferably 1 to 12, such as a unsubstituted ureide group, a methylureide group and a phenylureide group; phosphoric amide groups, the number of carbon atom thereof being preferably 1 to 30, more preferably 1 to 20, particularly preferably 1 to 12, such as a diethylphosphoric amide group and a phenylphosphoric amide group; a hydroxyl group; a mercapto group; halogen atoms such as a fluorine atom, a chlorine atom, a bromine atom and an iodine atom; a cyano group; a sulfo group; a carboxyl group; a nitro group; a hydroxamic acid group; a sulfino group; a hydrazino group; an imino group; heterocyclic groups that may have a nitrogen atom, an oxygen atom, a sulfur atom, etc. as a hetero atom, the number of carbon atom thereof being preferably 1 to 30, more preferably 1 to 12, such as an imidazolyl group, a pyridyl group, a quinolyl group, a furyl group, a thienyl group, a piperidyl group, a morpholino group, a benzoxazolyl group, a benzimidazolyl group, a benzthiazolyl group, a carbazolyl group and an azepinyl group; silyl groups, the number of carbon atom thereof being preferably 3 to 40, more preferably 3 to 30, particularly preferably 3 to 24, such as a trimethylsilyl group and a triphenylsilyl group; etc. The substituent may be further substituted.

$R_{11}$ is preferably an alkyl group, an alkenyl group, an alkynyl group, an aryl group, an amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a halogen atom, a cyano group or a heterocyclic group, more preferably an alkyl group, an alkenyl group, an aryl group, an alkoxy group, an aryloxy group, a halogen atom, a cyano group or a heterocyclic group, furthermore preferably an alkyl group, an aryl group, an alkoxy group, an aryloxy group or an aromatic heterocyclic group, particularly preferably an alkyl group, an aryl group, an alkoxy group or an aryloxy group, the most preferably an alkyl group, an alkoxy group or an aryloxy group.

In the formula (I), $R_{12}$ represents a hydrogen atom, an aliphatic hydrocarbon group, an aryl group or a heterocyclic group.

The aliphatic hydrocarbon group of $R_{12}$ is preferably selected from the group consisting of: alkyl groups, the number of carbon atom thereof being preferably 1 to 20, more preferably 1 to 12, particularly preferably 1 to 8, such as a methyl group, an ethyl group, an isopropyl group, a t-butyl group, a n-octyl group, a n-decyl group, a n-hexadecyl group, a cyclopropyl group, a cyclopentyl group and a cyclohexyl group; alkenyl groups, the number of carbon atoms thereof being preferably 2 to 20, more preferably 2 to 12, particularly preferably 2 to 8, such as a vinyl group, an allyl group, a 2-butenyl group and a 3-pentenyl group; and alkynyl groups, the number of carbon atoms thereof being preferably 2 to 20, more preferably 2 to 12, particularly preferably 2 to 8, such as a propargyl group and a 3-pentynyl group. The aliphatic hydrocarbon group is preferably an alkyl group or an alkenyl group.

The aryl group of $R_{12}$ is preferably has 6 to 30 carbon atoms, more preferably has 6 to 20 carbon atoms, particularly preferably has 6 to 12 carbon atoms. Examples of the aryl group include a phenyl group, a 2-methylphenyl group, a 3-methylphenyl group, a 4-methylphenyl group, a 4-methoxyphenyl group, a 3-trifluoromethylphenyl group, a pentafluorophenyl group, a 2-biphenylyl group, a 3-biphenylyl group, a 4-biphenylyl group, a 1-naphtyl group, a 2-naphtyl group, a 1-pyrenyl group, etc. Among the groups, preferred are a phenyl group, a 2-methylphenyl group, a 3-methylphenyl group, a 3-trifluoromethylphenyl group, a pentafluorophenyl group, a 2-biphenylyl group, a 4-biphenylyl group, a 1-naphtyl group, a 2-naphtyl group and a 1-pyrenyl group, more preferred are a phenyl group, a 2-methylphenyl group, a 2-biphenylyl group, a 4-biphenylyl group and a 2-naphtyl group, particularly preferred are a phenyl group, a 2-methylphenyl group, a 2-biphenylyl group and a 2-naphtyl group, the most preferred are a phenyl group.

The heterocyclic group of $R_{12}$ is preferably has 1 to 20 carbon atom, more preferably has 1 to 12 carbon atom, particularly preferably has 2 to 10 carbon atoms. The heterocyclic group may have a monocyclic structure or a polycyclic structure such as a condensed ring and a ring assemblage. The heterocyclic group is preferably an aromatic heterocyclic group comprising at least one hetero atom selected from the group consisting of a nitrogen atom, an oxygen atom, a sulfur atom and a selenium atom. The heterocyclic group may have a structure of a pyrrolidine ring, a piperidine ring, a pyrrole ring, a furan ring, a thiophene ring, an imidazoline ring, an imidazole ring, a benzimidazole ring, a naphthoimidazole ring, a thiazolidine ring, a thiazole ring, a benzthiazole ring, a naphthothiazole ring, an isothiazole ring, an oxazoline ring, an oxazole ring, a benzoxazole ring, a naphthoxazole ring, an isoxazole ring, a selenazole ring, a benzselenazole ring, a naphthoselenazole ring, a pyridine ring, a quinoline ring, an isoquinoline ring, an indole ring, an indolenine ring, a pyrazole ring, a pyrazine ring, a pyrimidine ring, a pyridazine ring, a triazine ring, an indazole ring, a purine ring, a phthalazine ring, a naphthylizine ring, a quinoxaline ring, a quinazoline ring, a cinnoline ring, a pteridine ring, a phenanthridine ring, a pteridine ring, a phenanthroline ring, a tetrazaindene ring, etc. Among them, preferred are a furan ring, a thiophene ring, a pyridine ring, a quinoline ring, a pyrazine ring, a pyrimidine ring, a pyridazine ring, a triazine ring, a phthalazine ring, a naphthylizine ring, a quinoxaline ring and a quinazoline ring, more preferred are a furan ring, a thiophene ring, a pyridine ring, a quinoline ring and a triazine ring, particularly preferred are a quinoline ring and a triazine ring.

In the case where $R_{12}$ is an aliphatic hydrocarbon group, an aryl group or a heterocyclic group, the groups may have a substituent with examples and preferred embodiments being the same as those of $R_{11}$. $R_{12}$ is preferably an alkyl group, an aryl group or an aromatic heterocyclic group, more preferably an aryl group or an aromatic heterocyclic group, particularly preferably an aryl group or an aromatic heterocyclic group having a 6-membered ring structure.

In the formula (I), $R_{13}$ represents a hydrogen atom or a substituent with examples being the same as those of $R_{11}$. $R_{13}$ is preferably a hydrogen atom, an alkyl group, an alkenyl group, an alkynyl group, an aryl group, a halogen atom or a heterocyclic group, more preferably a hydrogen atom, an alkyl group, an aryl group or a heterocyclic group, furthermore preferably a hydrogen atom, an alkyl group, an aryl group or an aromatic heterocyclic group, particularly preferably a hydrogen atom, an alkyl group or an aryl group, further particularly preferably a hydrogen atom or an alkyl group, the most preferably a hydrogen atom.

In the formula (I), n is an integer of 0 to 2, preferably 0 or 1, more preferably 0. When n is 2, a plurality of $R_{11}$'s may be the same or different substituents and may bond together to form a ring.

In the formula (I), L represents a single bond or a linking group. L bonds to a position of a purine skeleton, to which $R_{11}$, $R_{12}$ or $R_{13}$ may be attached. Thus, $R_{11}$, $R_{12}$ and $R_{13}$ may be substituted by L. L is preferably a single bond or a linking group composed of C, H, N, O, S, Si and/or Ge, more preferably a single bond or a linking group selected from the group consisting of alkylene groups, alkenylene groups, alkynylene groups, arylene groups, multi-valent heterocyclic groups and combinations of the groups and N, O or S, particularly preferably a single bond or a linking group selected from the group consisting of alkylene groups, arylene groups, aryltriyl groups, multi-valent aromatic heterocyclic groups and combinations of the groups and N, O or S. The multi-valent aromatic heterocyclic group preferably has an azole ring, a thiophene ring or a furan ring.

The linking group of L may have a substituent with examples being the same as those of $R_{11}$. The substituent on L is preferably an alkyl group, an alkenyl group, an alkynyl group, an aryl group, an alkoxy group, an aryloxy group, an acyl group, a halogen atom, a cyano group, a heterocyclic group or a silyl group, more preferably an alkyl group, an alkenyl group, an alkynyl group, an aryl group, an alkoxy group, an aryloxy group, a halogen atom, a cyano group or an aromatic heterocyclic group, particularly preferably an alkyl group, an aryl group or an aromatic heterocyclic group.

Specific examples of the linking group represented by L will be illustrated below without intention of restricting the scope of the present invention defined by the claims attached hereto.

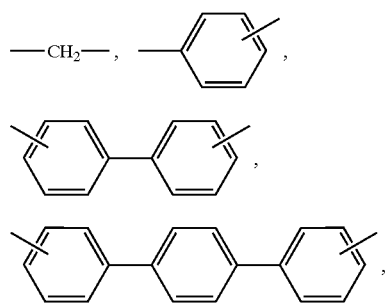

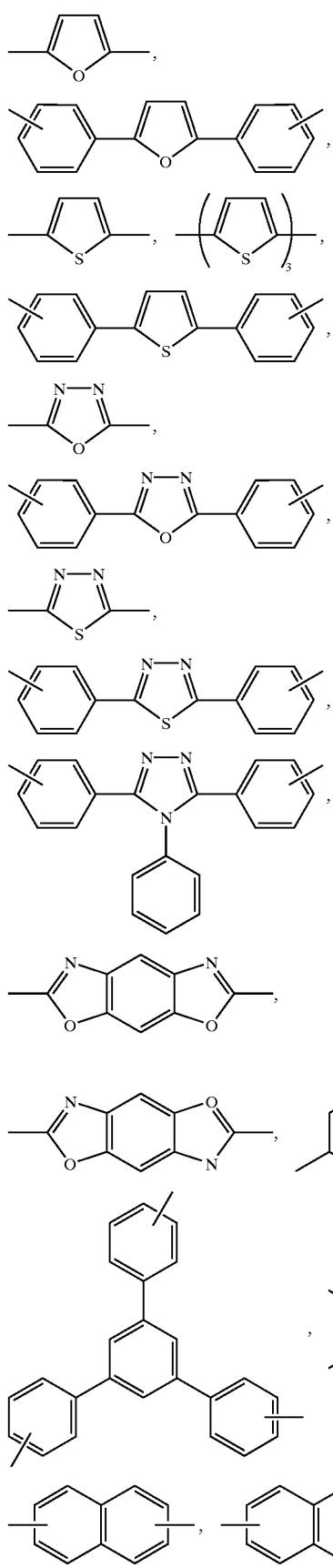
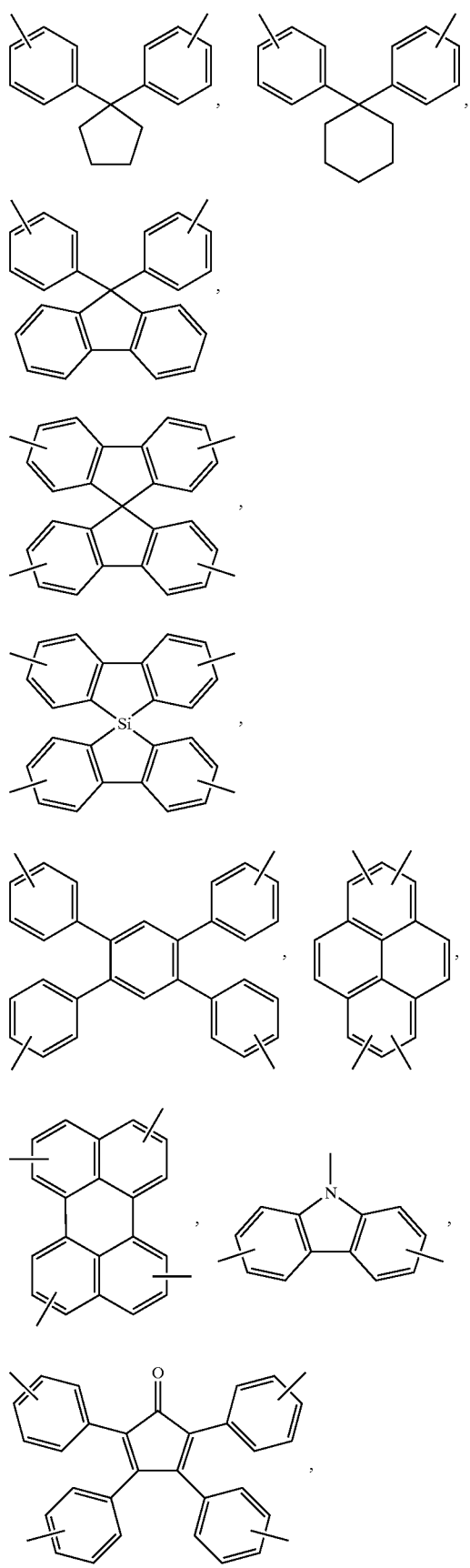

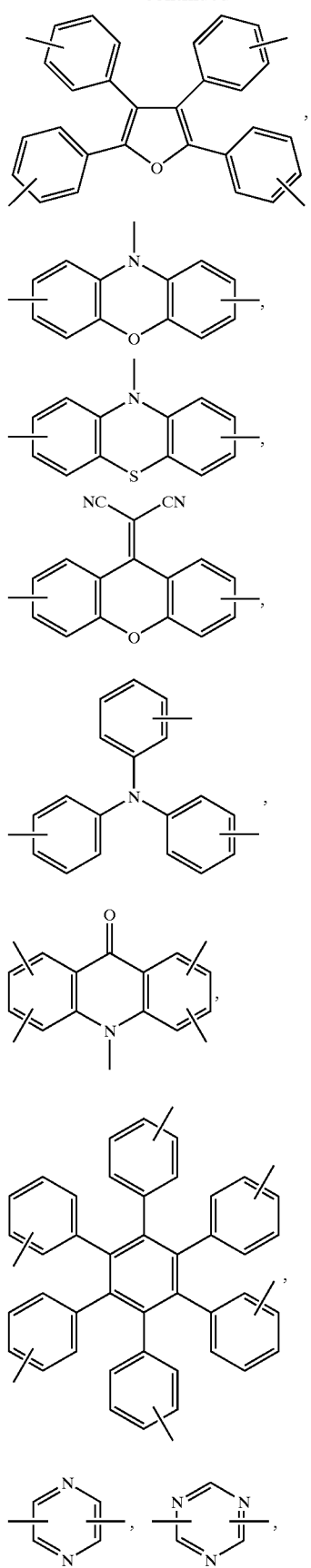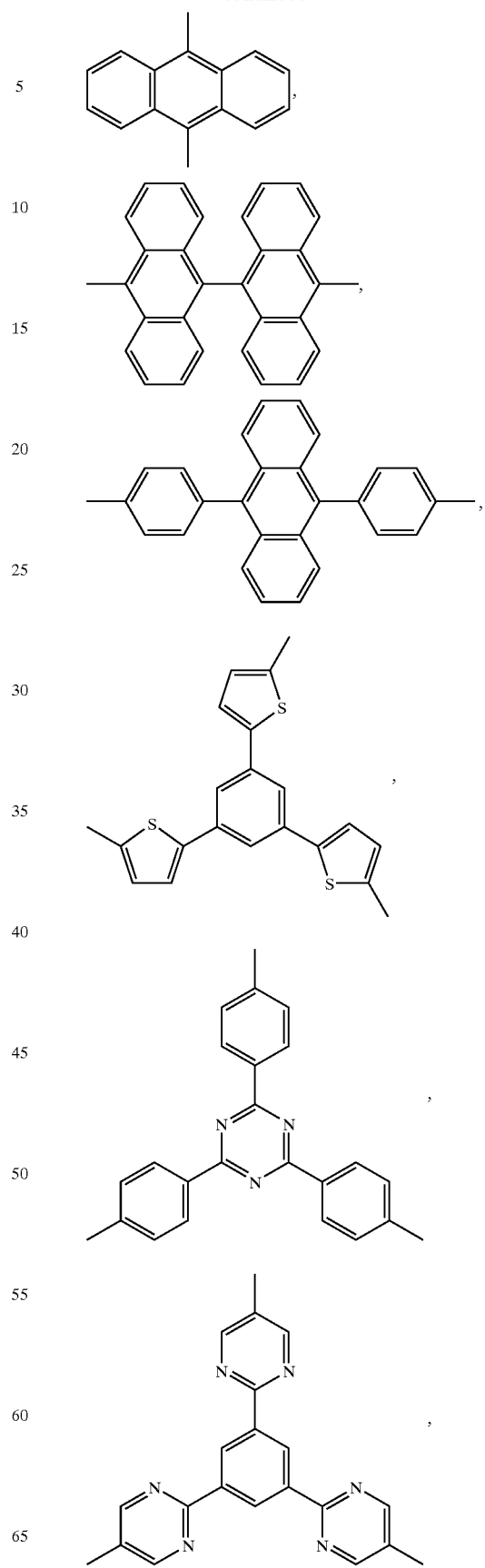

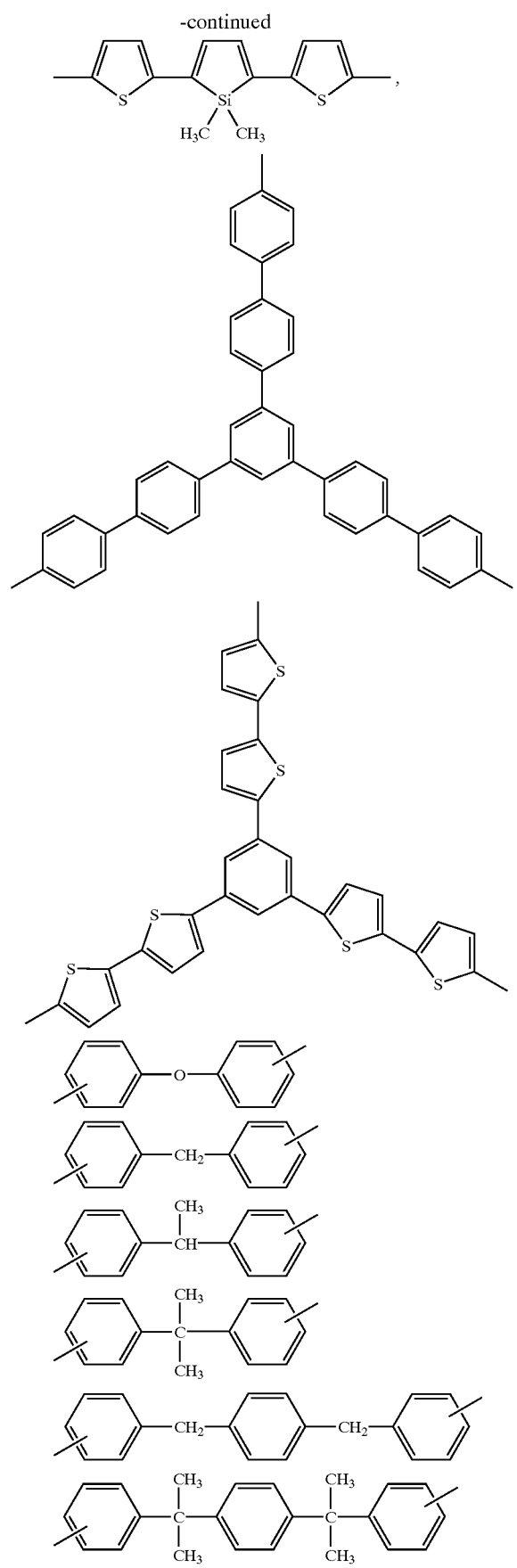
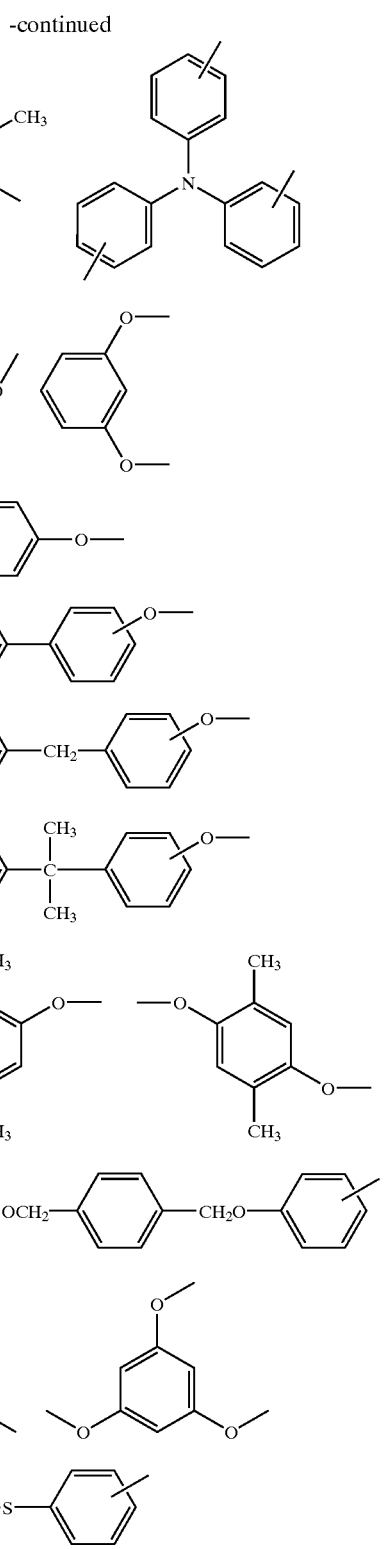
In the formula (I), m is an integer of 2 or more, preferably an integer of 2 to 8, more preferably an integer of 2 to 6, furthermore preferably an integer of 2 to 4, particularly preferably 2 or 3, the most preferably 2.
The compound (I) is preferably represented by any one of the following formulae (II) and (XI), more preferably represented by the following formula (XI).

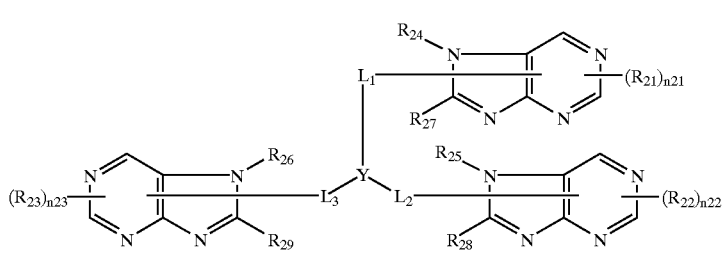

Formula (II)

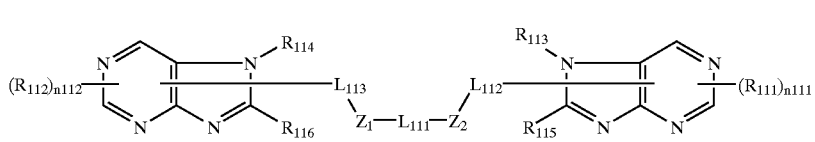

Formula (XI)

In the formula (II), $R_{21}$, $R_{22}$ and $R_{23}$ are the same as above-mentioned $R_{11}$ with respect to meaning and preferred embodiments, respectively. $R_{24}$, $R_{25}$ and $R_{26}$ are the same as above-mentioned $R_{12}$ with respect to meaning and preferred embodiments, respectively. $R_{27}$, $R_{28}$ and $R_{29}$ are the same as above-mentioned $R_{13}$ with respect to meaning and preferred embodiments, respectively. Further, n21, n22 and n23 are the same as above-mentioned n with respect to meaning and preferred embodiments, respectively.

In the formula (II), $L_1$, $L_2$ and $L_3$ have the same meaning as above-mentioned L, respectively. $L_1$, $L_2$ and $L_3$ are preferably a single bond or a linking group selected from the group consisting of arylene groups, divalent aromatic heterocyclic groups and combinations thereof, more preferably a single bond or a linking group selected from the group consisting of divalent aromatic heterocyclic groups comprising a benzene ring, a naphthalene ring, an anthracene ring, a pyridine ring, a pyrazine ring, a thiophene ring, a furan ring, an oxazole ring, a thiazole ring, an oxathiazole ring, a thiadiazole ring or a triazole ring and combinations thereof, furthermore preferably a single bond or a linking group selected from the group consisting of divalent aromatic heterocyclic groups comprising a benzene ring or a thiophene ring and combinations thereof, particularly preferably a single bond or a linking group selected from the group consisting of divalent aromatic heterocyclic groups comprising a benzene ring and combinations thereof, the most preferably a single bond, respectively. The linking group of $L_1$, $L_2$ and $L_3$ may have a substituent with examples being the same as those of $R_{11}$.

In the formula (II), Y represents a nitrogen atom or a 1,3,5-benzenetriyl group. The 1,3,5-benzenetriyl group may have a substituent at 2-, 4- and/or 6-position, and the substituent may be an alkyl group, an aryl group, a halogen atom, etc. Y is preferably a nitrogen atom or an unsubstituted 1,3,5-benzenetriyl group, more preferably an unsubstituted 1,3,5-benzenetriyl group.

In the formula (XI), $R_{111}$ and $R_{112}$ are the same as above-mentioned $R_{11}$ with respect to meaning and preferred embodiments, respectively. $R_{113}$ and $R_{114}$ are the same as above-mentioned $R_{12}$ with respect to meaning and preferred embodiments, respectively. $R_{115}$ and $R_{116}$ are the same as above-mentioned $R_{13}$ with respect to meaning and preferred embodiments, respectively. Further, n111 and n112 are the same as above-mentioned n with respect to meaning and preferred embodiments, respectively.

In the formula (XI), $Z_1$ and $Z_2$ represent an arylene group or a divalent aromatic heterocyclic group, respectively. $Z_1$ and $Z_2$ are preferably a divalent linking group comprising a benzene ring, a naphthalene ring, an anthracene ring, a pyridine ring, a pyrazine ring, a thiophene ring, a furan ring, an oxazole ring, a thiazole ring, an oxadiazole ring, a thiadiazole ring or a triazole ring, more preferably a divalent linking group comprising a benzene ring, a naphthalene ring, an anthracene ring, a pyridine ring, a thiophene ring, a furan ring, an oxazole ring or a thiazole ring, furthermore preferably a divalent linking group comprising a benzene ring, a naphthalene ring, a thiophene ring or a furan ring, particularly preferably a phenylene group or a naphtylene group, the most preferably a phenylene group, respectively.

In the formula (XI), $L_{111}$ has the same meaning as above-mentioned L. $L_{111}$ is preferably a single bond or a linking group composed of C, H, N, O, S, Si and/or Ge, more preferably a single bond or a linking group selected from the group consisting of alkylene groups, alkenylene groups, alkynylene groups, arylene groups, divalent heterocyclic groups and combinations thereof, furthermore preferably a single bond or a linking group selected from the group consisting of alkylene groups, arylene groups, divalent heterocyclic groups and combinations thereof, particularly preferably an alkylene group or a linking group of a combination of an alkylene group and an arylene group.

In the formula (XI), $L_{112}$ and $L_{113}$ represent a single bond, —O—, —S— or —N($R_{117}$)—, respectively. $R_{117}$ is the same as above-mentioned $R_{12}$ with respect to meaning and preferred embodiments. $L_{112}$ and $L_{113}$ are preferably a single bond or —O—, respectively. $R_{117}$ is preferably a hydrogen atom, an alkyl group, an aryl group or an aromatic heterocyclic group, more preferably a hydrogen atom or an alkyl group, particularly preferably an alkyl group. $L_{112}$ bonds to a position of a purine skeleton, to which $R_{111}$, $R_{113}$ or $R_{115}$ may be attached, and $L_{113}$ bonds to a position of a purine skeleton, to which $R_{112}$, $R_{114}$ or $R_{116}$ may be attached. Thus, $R_{111}$, $R_{113}$ and $R_{115}$ may be substituted by $L_{112}$ and $R_{112}$, $R_{114}$ and $R_{116}$ may be substituted by $L_{113}$.

The compound represented by the formula (II) is preferably represented by any one of the following formulae (III) and (IV), particularly preferably represented by the following formula (IV). The compound represented by the formula (XI) is preferably represented by any one of the following formulae (XII) and (XIII). The heterocyclic compound of the present invention represented by the formula (III), (IV), (XII) or (XIII) has a wide applicability for an electronic device, etc.

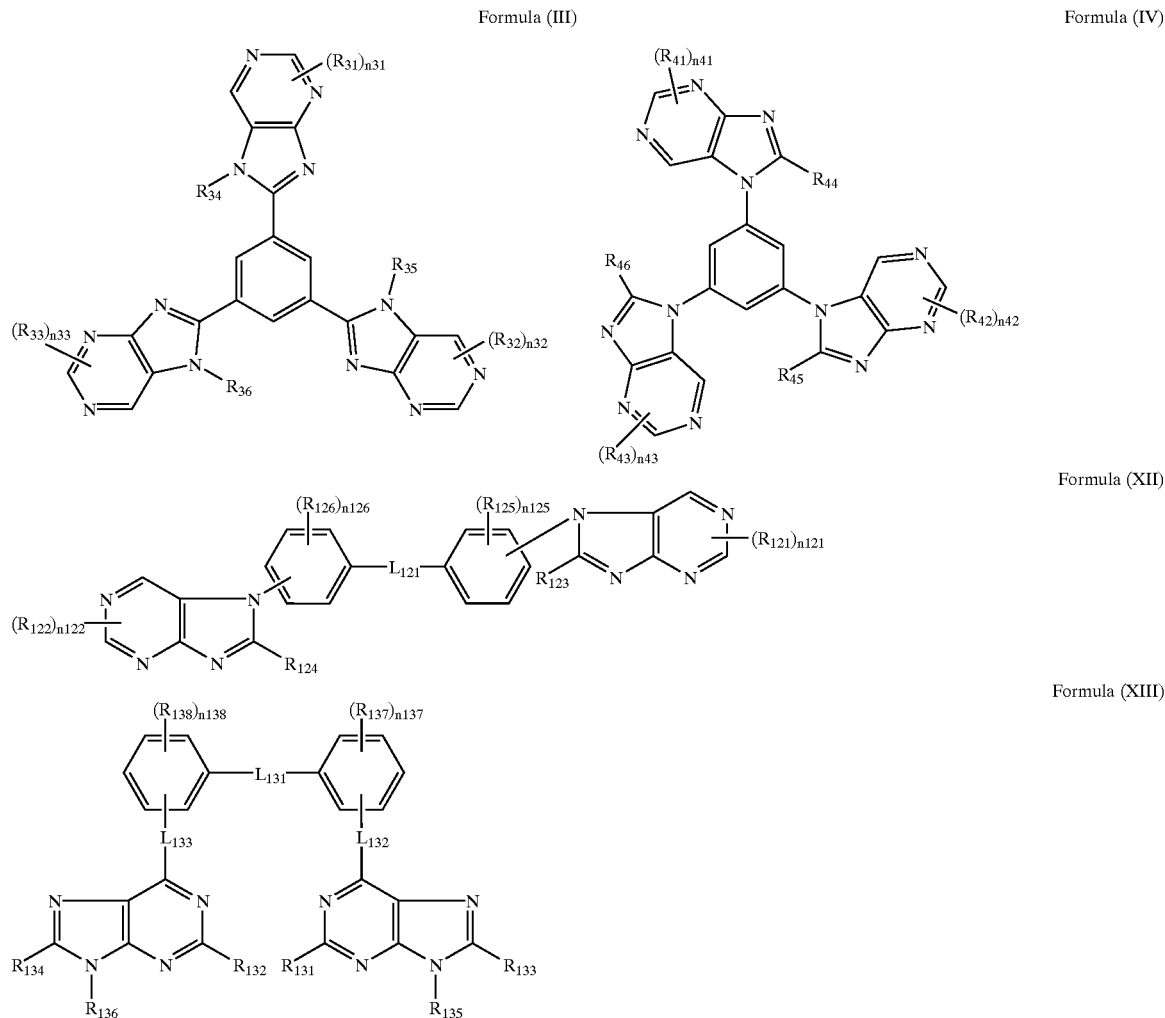

Formula (III)

Formula (IV)

Formula (XII)

Formula (XIII)

In the formula (III), $R_{31}$, $R_{32}$ and $R_{33}$ are the same as above-mentioned $R_{11}$ with respect to meaning and preferred embodiments, respectively. $R_{34}$, $R_{35}$ and $R_{36}$ are the same as above-mentioned $R_{12}$ with respect to meaning and preferred embodiments, respectively. Further, n31, n32 and n33 are the same as above-mentioned mentioned n with respect to meaning and preferred embodiments, respectively.

In the formula (IV), $R_{41}$, $R_{42}$ and $R_{43}$ are the same as above-mentioned $R_{11}$ with respect to meaning and preferred embodiments, respectively. $R_{44}$, $R_{45}$ and $R_{46}$ are the same as above-mentioned $R_{13}$ with respect to meaning and preferred embodiments, respectively. Further, n41, n42 and n43 are the same as above-mentioned n with respect to meaning and preferred embodiments, respectively.

In the formula (XII), $R_{121}$ and $R_{122}$ are the same as above-mentioned $R_{11}$ with respect to meaning and preferred embodiments, respectively. $R_{123}$ and $R_{124}$ are the same as above-mentioned $R_{13}$ with respect to meaning and preferred embodiments, respectively. $R_{125}$ and $R_{126}$ are the same as above-mentioned $R_{11}$ with respect to meaning and preferred embodiments, respectively. n121 and n122 are the same as above-mentioned n with respect to meaning and preferred embodiments, respectively. n125 and n126 are an integer of 0 to 4, preferably an integer of 0 to 2, more preferably 0 or 1, respectively. $L_{121}$ is the same as above-mentioned $L_{111}$ with respect to meaning and preferred embodiments.

In the formula (XIII), $R_{131}$ and $R_{132}$ are the same as above-mentioned $R_{11}$ with respect to meaning and preferred embodiments, respectively. $R_{133}$ and $R_{134}$ are the same as above-mentioned $R_{13}$ with respect to meaning and preferred embodiments, respectively. $R_{135}$ and $R_{136}$ are the same as above-mentioned $R_{12}$ with respect to meaning and preferred embodiments, respectively. $R_{137}$ and $R_{138}$ are the same as above-mentioned $R_{11}$ with respect to meaning and preferred embodiments, respectively. n137 and n138 are the same as above-mentioned n125 and n126 with respect to meaning and preferred embodiments, respectively. $L_{131}$ is the same as above-mentioned $L_{111}$ with respect to meaning and preferred embodiments. $L_{132}$ and $L_{133}$ represent a single bond, —O—, —S— or —N($R_{139}$)—, respectively. $R_{139}$ is the same as above-mentioned $R_{117}$ with respect to meaning and preferred embodiments. Thus, $L_{132}$ and $L_{133}$ are the same as above-mentioned $L_{112}$ and $L_{113}$ with respect to meaning and preferred embodiments, respectively.

The compound (I) may be such that acts as a hole-injecting material, a hole-transporting material, a light-emitting material, an electron-transporting material, an electron-injecting material, a host material, etc. The transition metal complex (1) may have a plurality of functions. In this invention, the compound (I) is preferably used as an electron-injecting material, an electron-transporting material and/or a host material. Concrete examples of the compound (I) will be illustrated below without intention of restricting the scope of the present invention defined by the claims attached hereto.

(E-1)
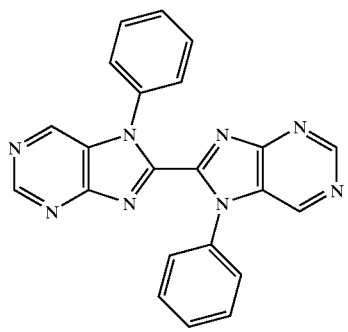
(E-2)
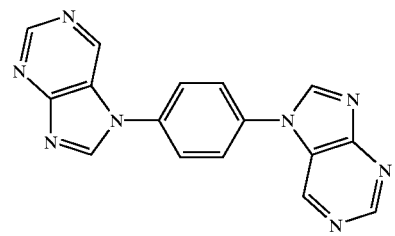
(E-3)
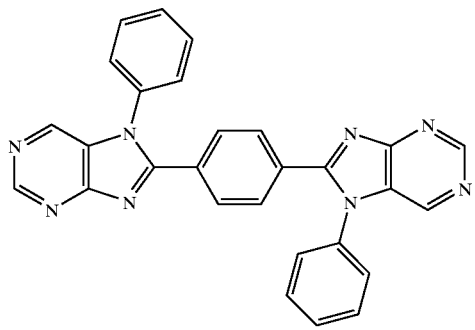
(E-4)
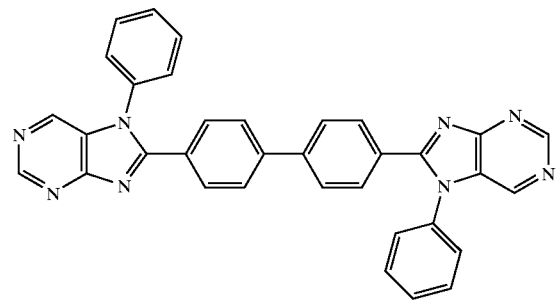
(E-5)
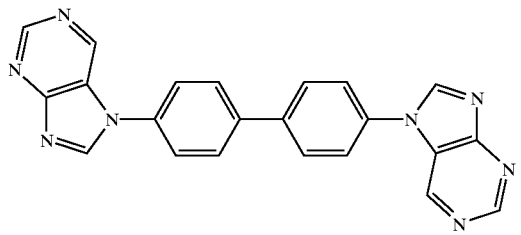
(E-6)
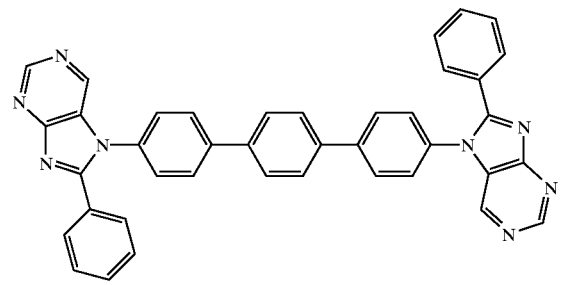
(E-7)
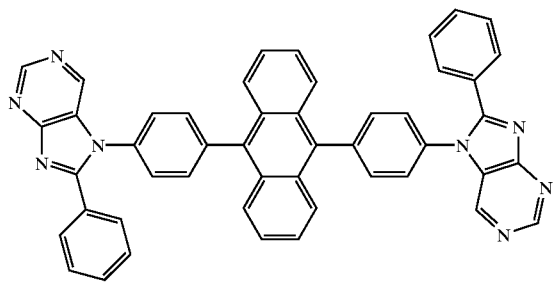
(E-8)
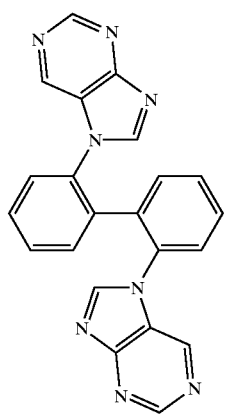

(E-9)
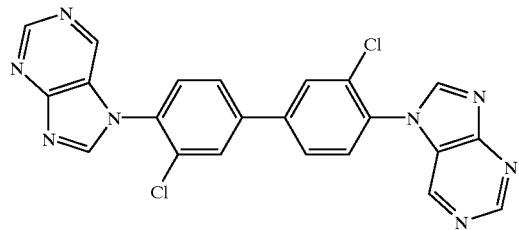
(E-10)
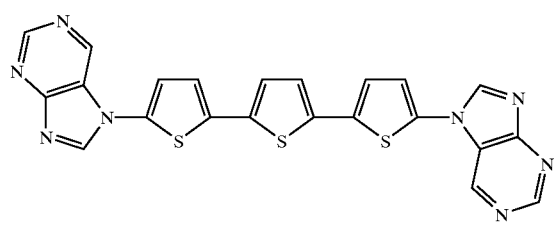
(E-11)
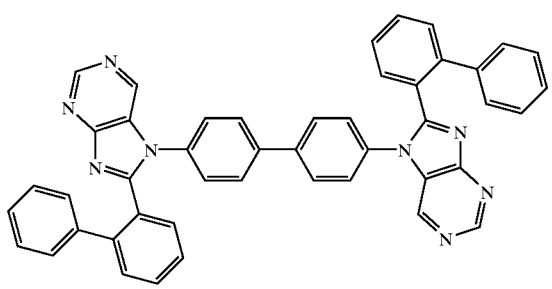
(E-12)
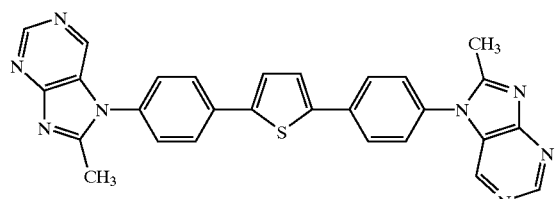
(E-13)
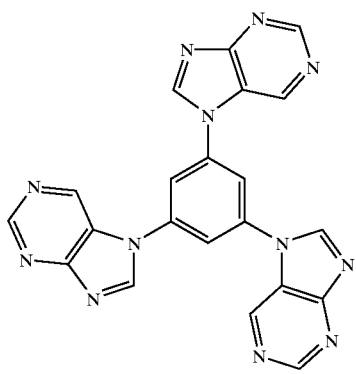
(E-14)
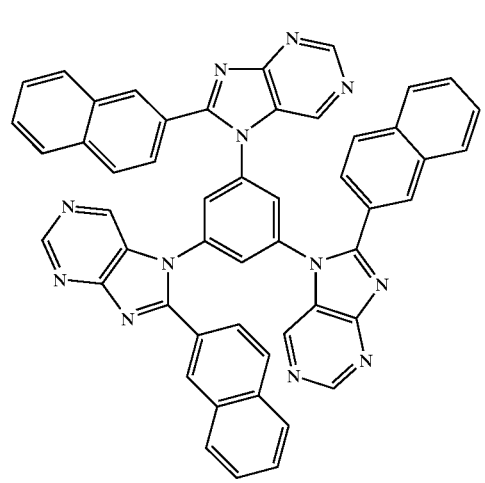
(E-15)
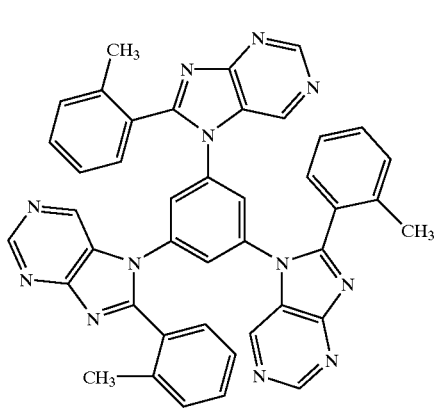

-continued
(E-16)
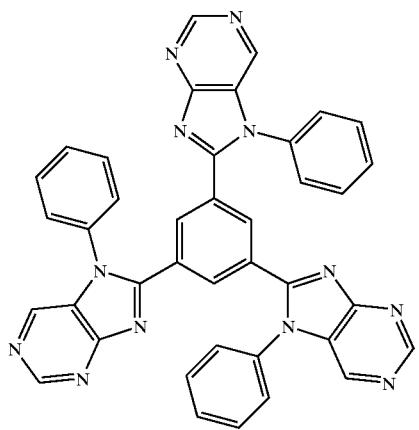
(E-17)
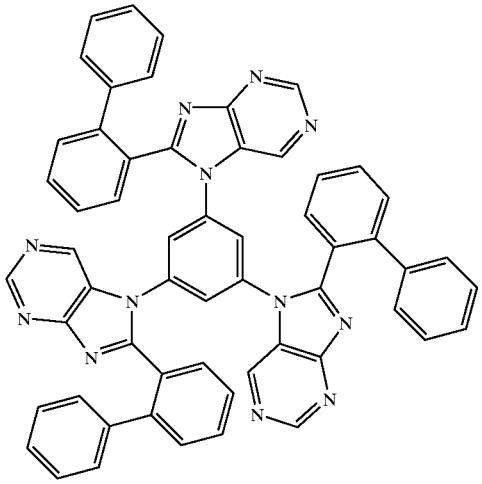
(E-18)
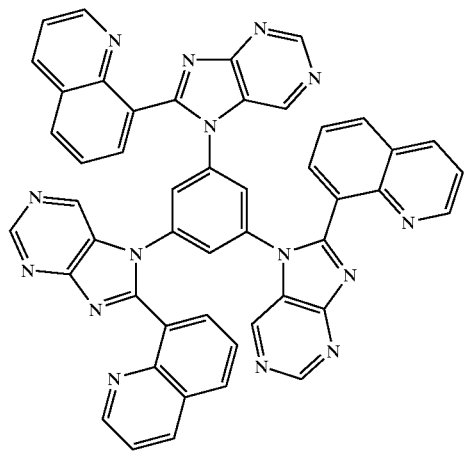
(E-19)
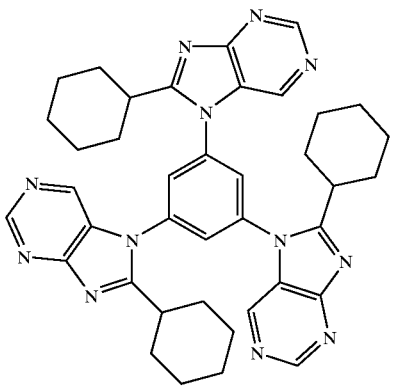
(E-20)
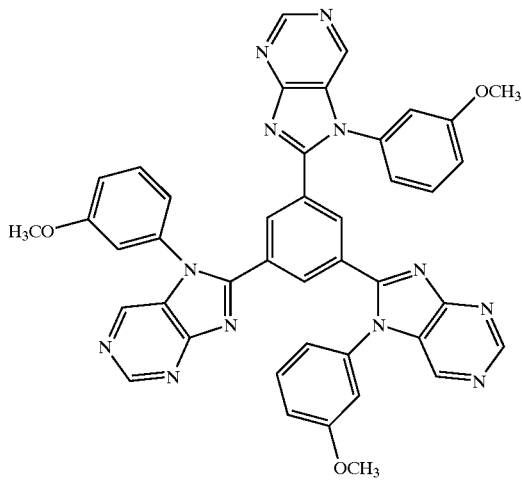
(E-21)
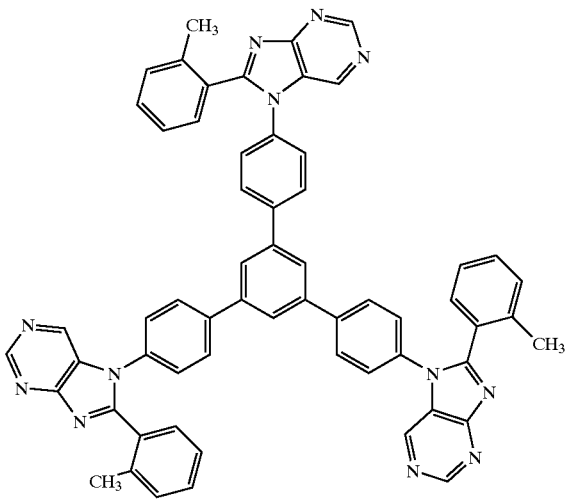

-continued
(E-22)
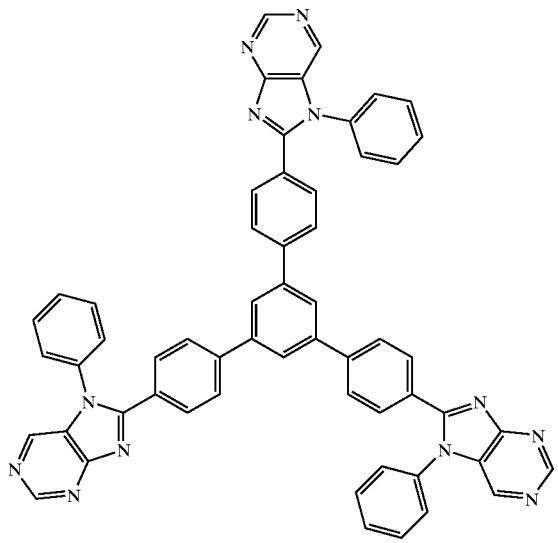
(E-23)
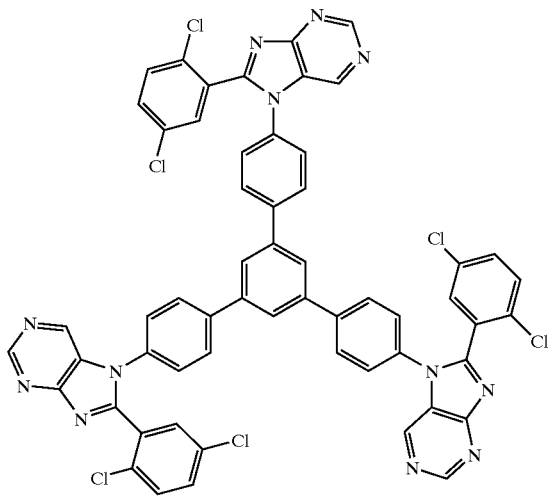
(E-24)
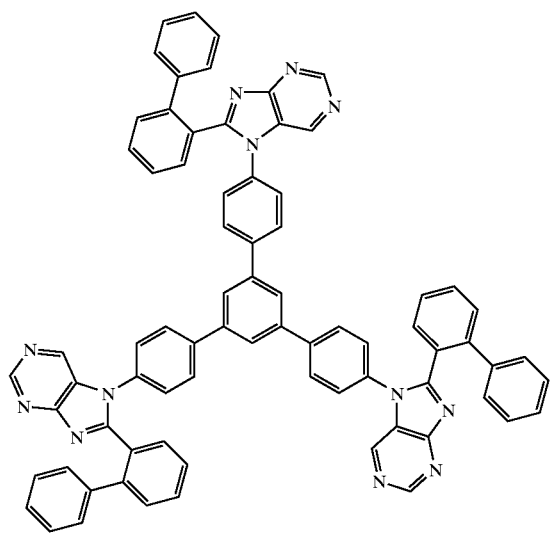
(E-25)
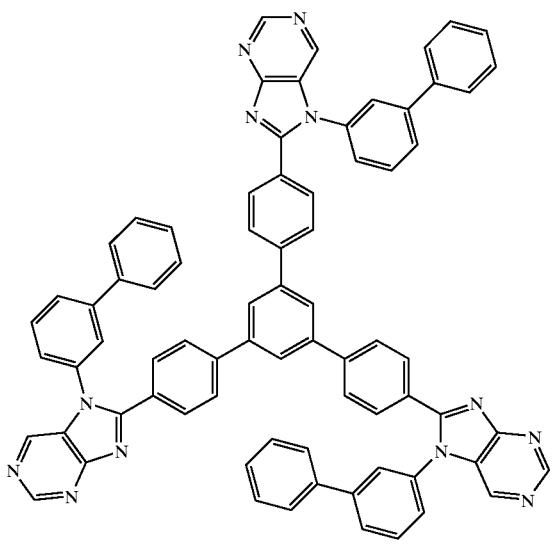
(E-26)
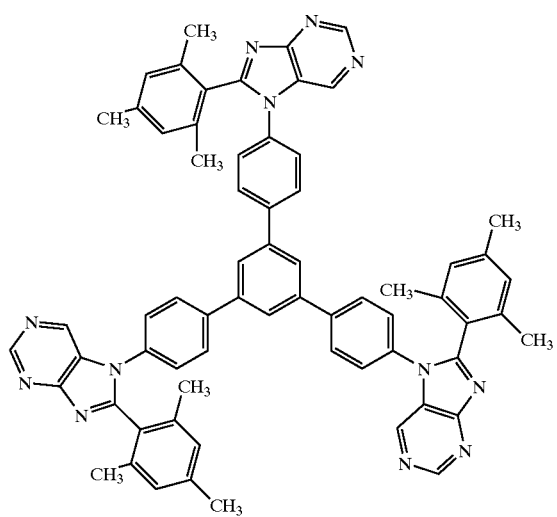
(E-27)
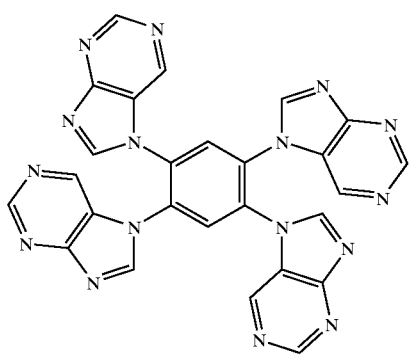

-continued
(E-28)
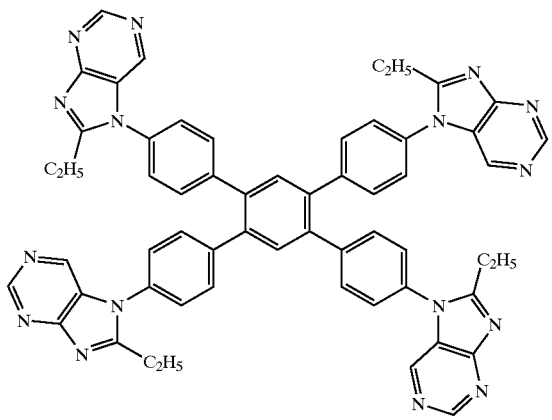
(E-29)
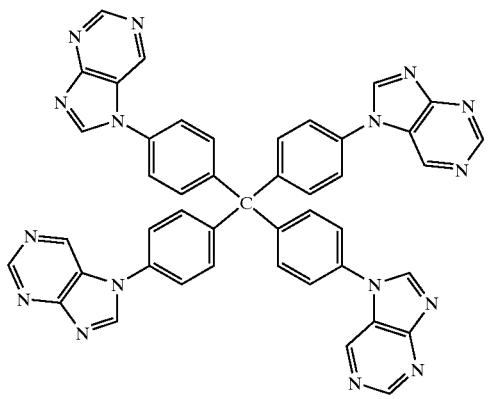
(E-30)
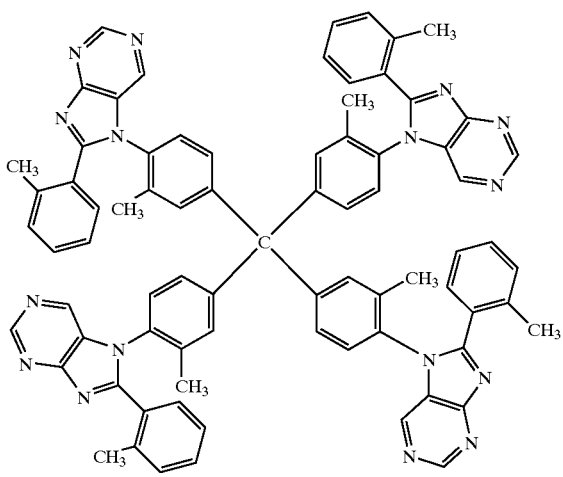
(E-31)
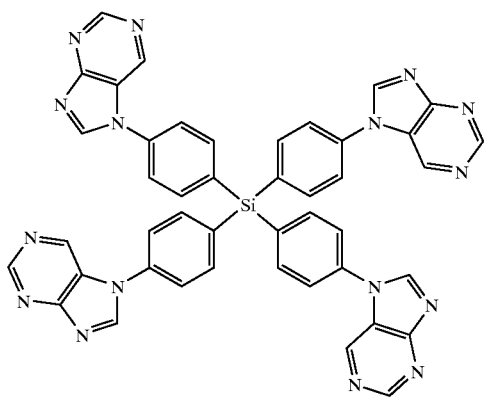
(E-32)
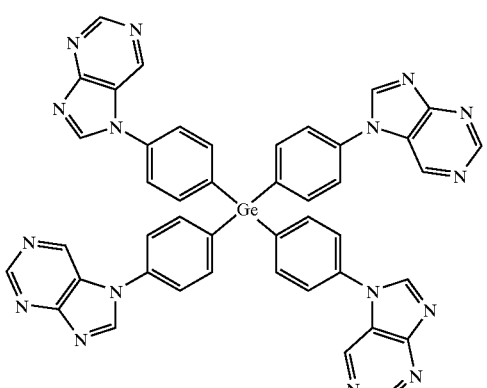
(E-33)
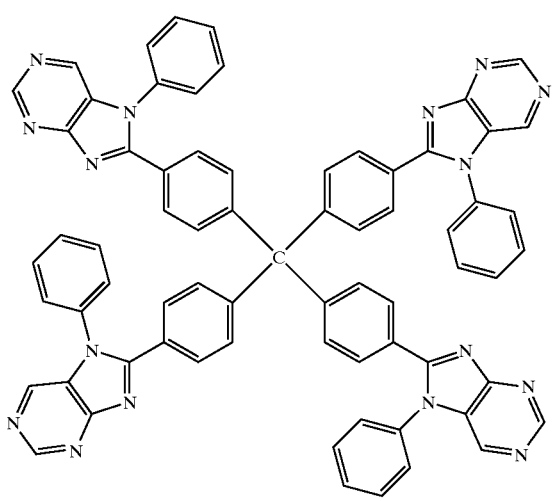

-continued
(E-34)
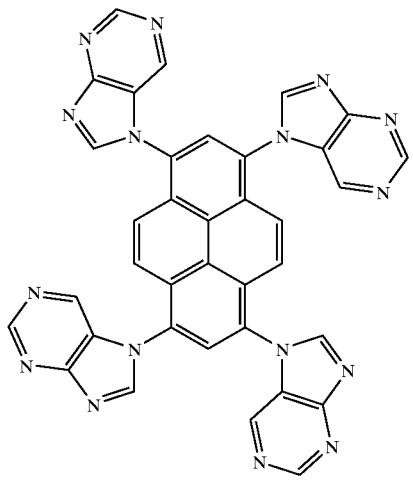
(E-35)
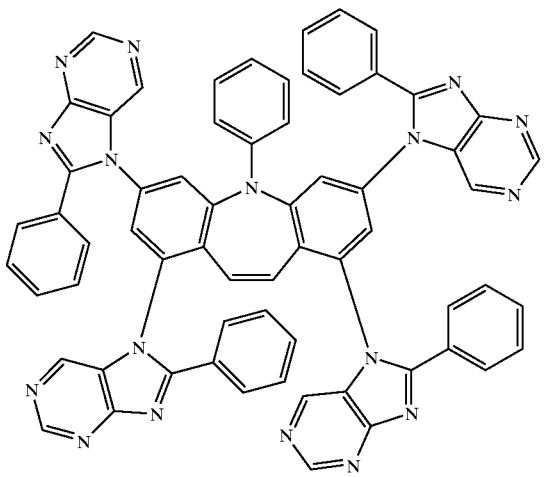
(E-36)
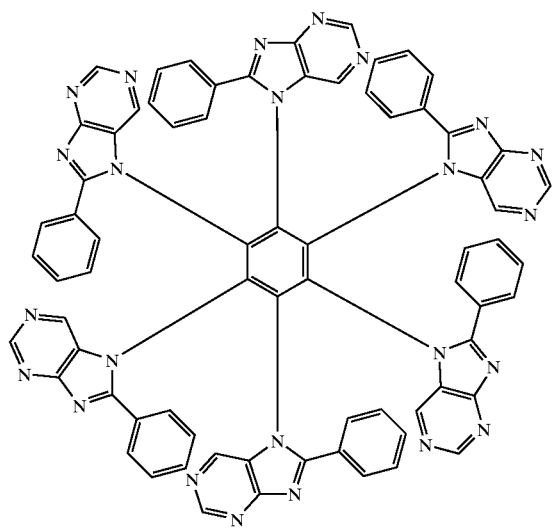
(E-37)
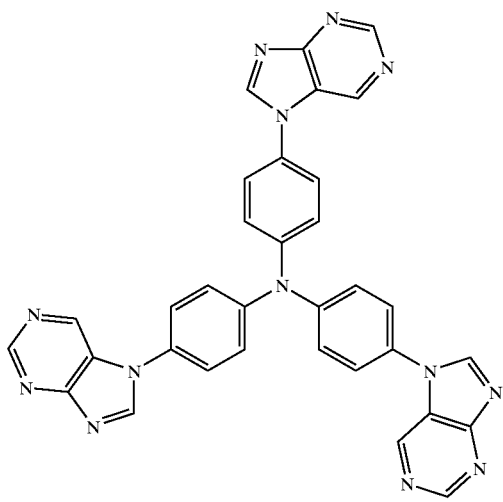
(E-38)
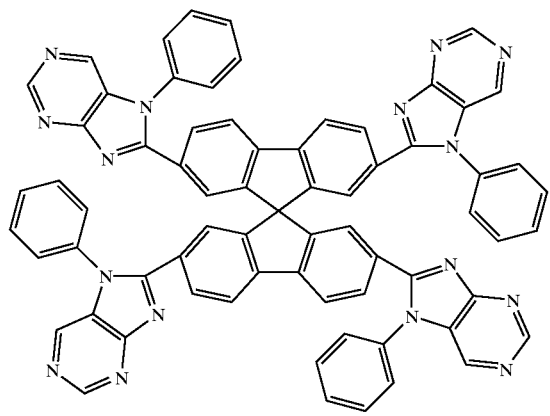
(E-39)
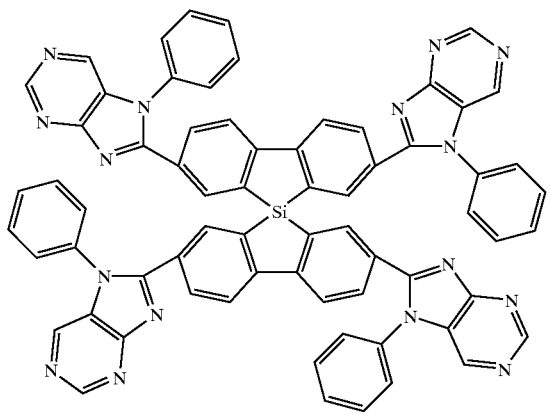

-continued
(E-40)
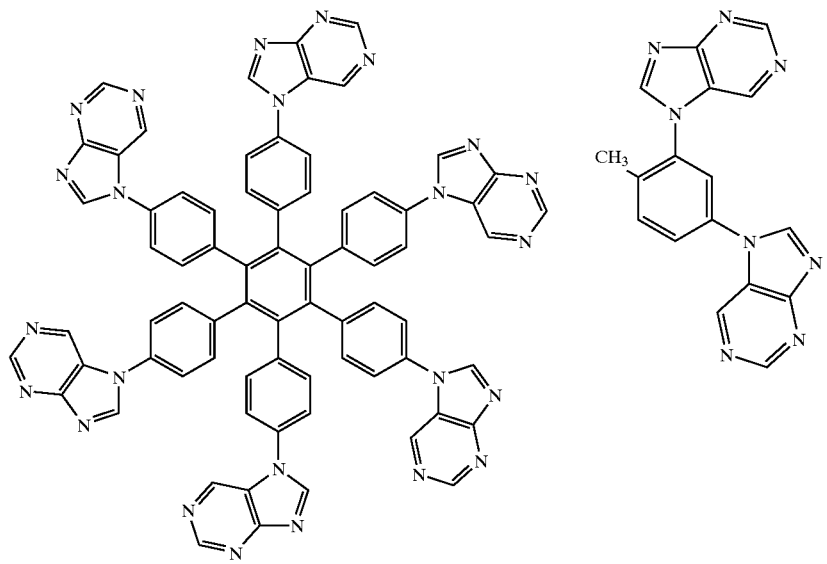
(E-41)
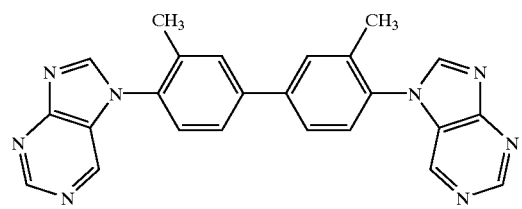
(E-42)
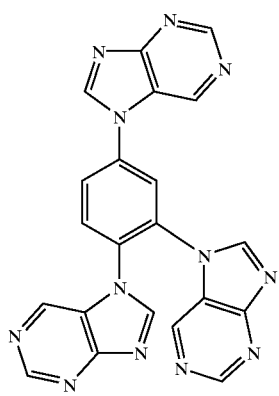
(E-43)
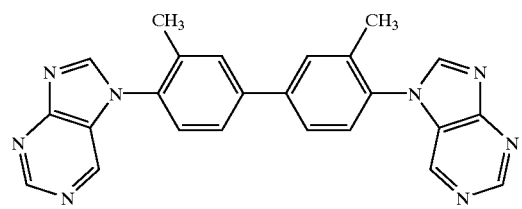
(E-44)
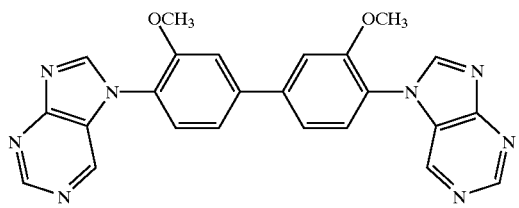
(E-45)
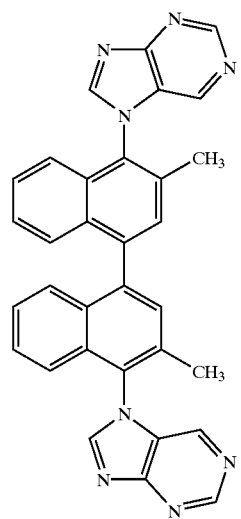

-continued
(E-46)
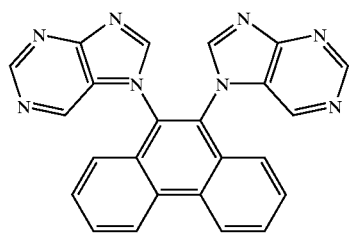
(E-47)
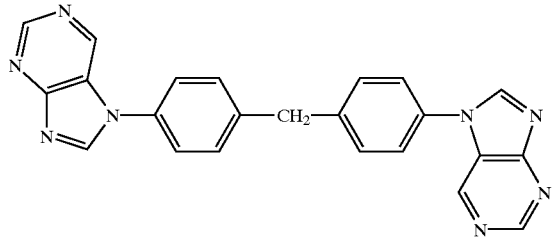
(E-48)
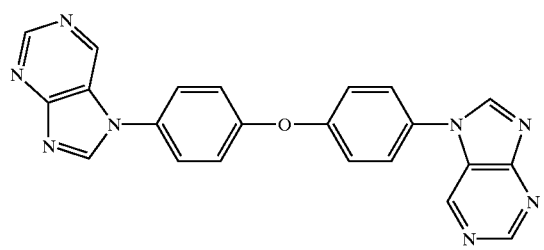
(E-49)
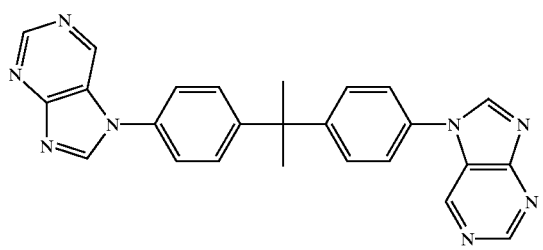
(E-50)
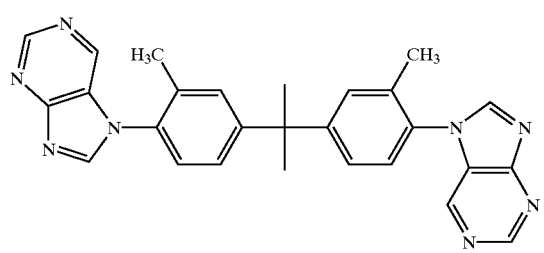
(E-51)
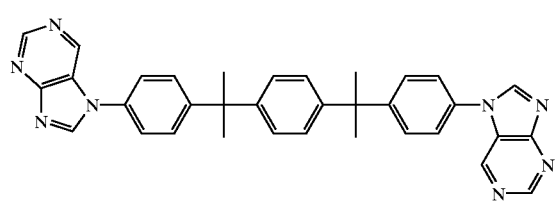
(E-52)
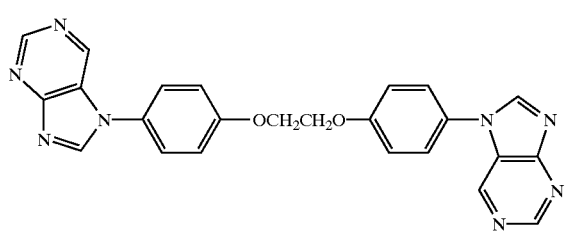
(E-53)
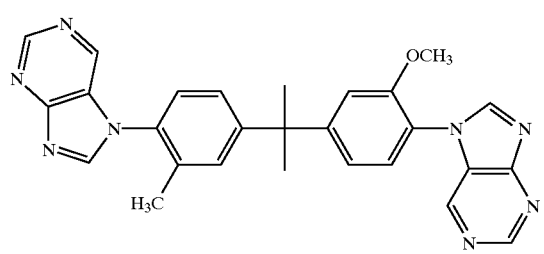
(E-54)
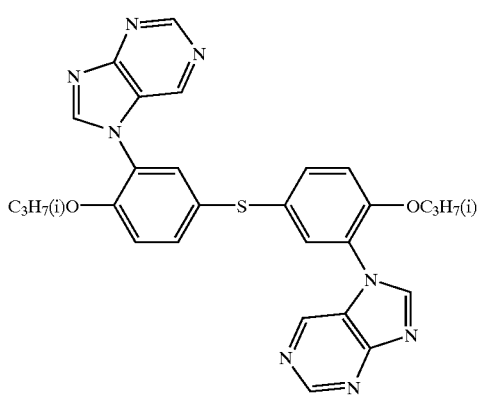

-continued
(E-55)
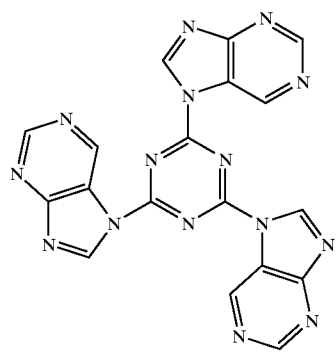
(E-56)
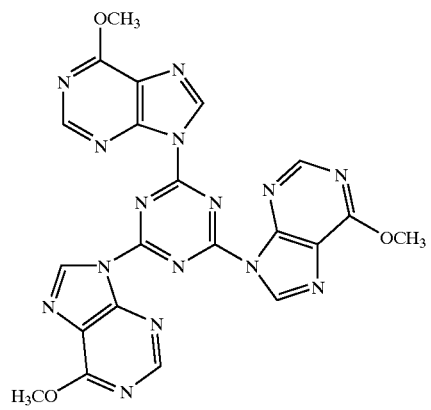
(E-57)
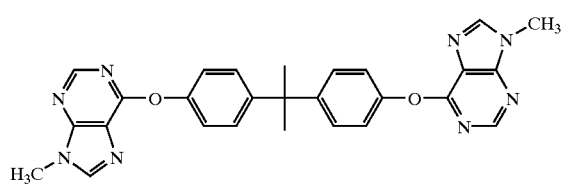
(E-58)
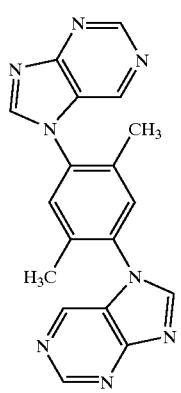
(E-59)
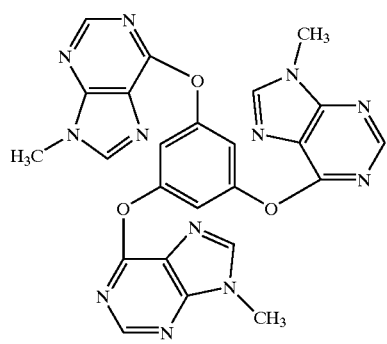
(E-60)
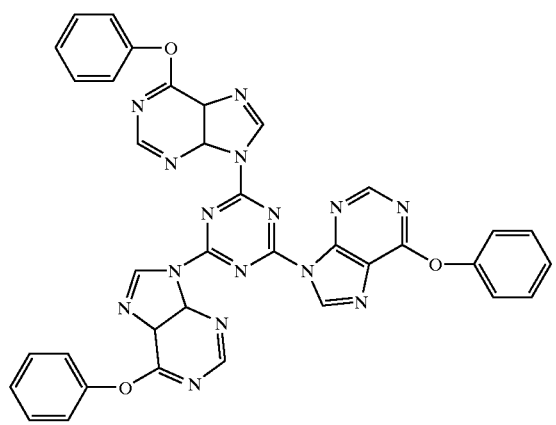
(E-61)
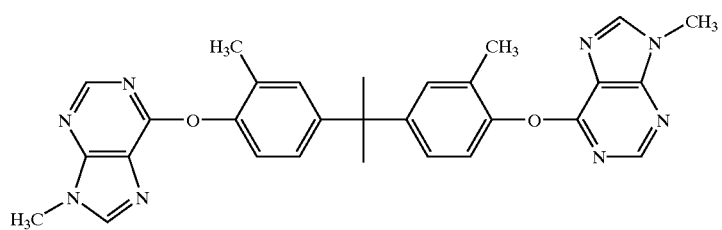

-continued

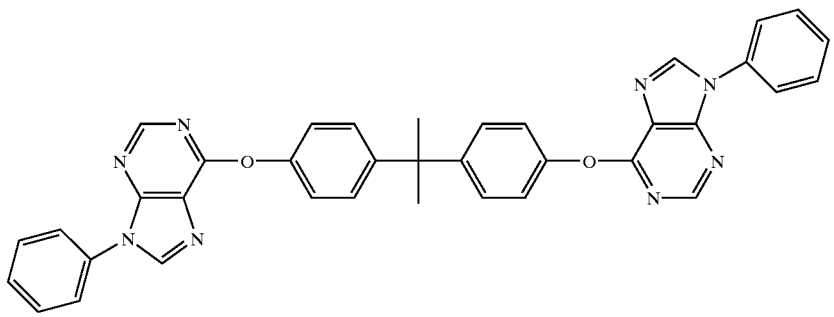
(E-62)

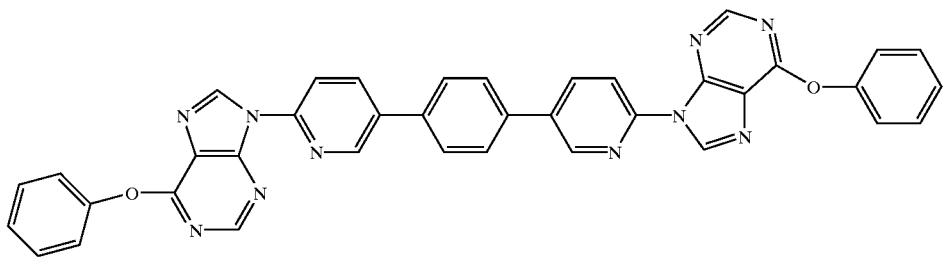
(E-63)

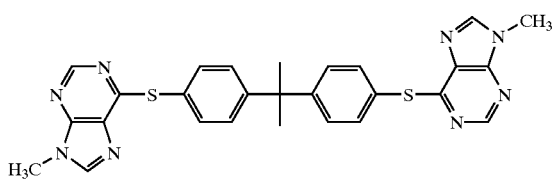
(E-65)

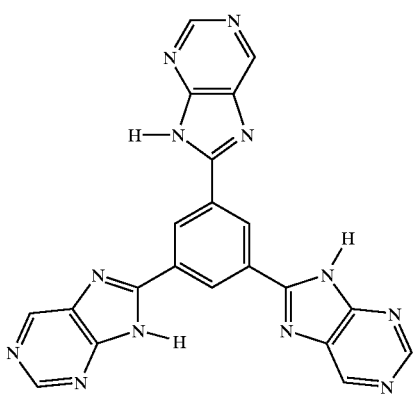
(E-64)

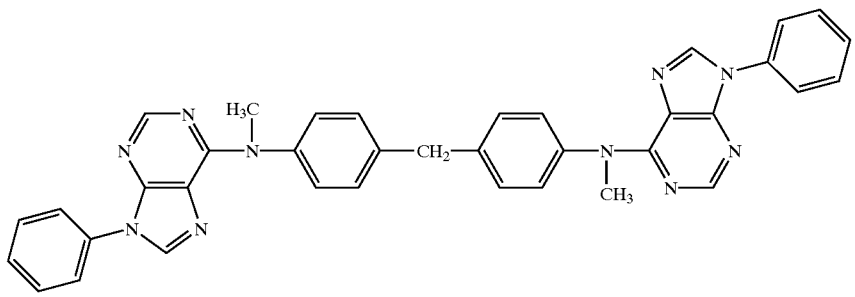
(E-66)

The compound (I) can be synthesized with reference to: Annalen der Chemie, Vol. 673, Page 82 (1964); Journal of the Chemical Society, Section C, Page 10 (1966); Chemische Berichte, Vol.100, Page 2280 (1967); Yakugaku Zassi (Journal of the Pharmaceutical Society of Japan), Vol. 99, Page 114 (1979); Journal of Heterocyclic Chemistry, Vol. 34, Page 1459 (1997); Journal of Organic Chemistry, Vol. 27, Page 986 (1962); Journal of Organic Chemistry, Vol. 48, Page 850 (1983); etc.

[2] Light-Emitting Device

The light-emitting device of the present invention comprises a pair of electrodes (positive electrode and negative electrode) and one or more organic layers disposed between the electrodes. The one or more organic layers comprises a light-emitting layer. At least one of the one or more organic layers comprises the compound (I). Although system utilizing the light-emitting device, a driving method therefor, use thereof, etc. are not particularly limited, the light-emitting device is preferably such that uses the compound (I) as an electron-injecting material, an electron-transporting material and/or a host material. An organic electroluminescence (EL) device is known as a typical light-emitting device.

In the case of using the compound (I) as the host material, weight ratio of the compound (I) is preferably 1 to 99 weight %, more preferably 25 to 98 weight %, particularly preferably 65 to 98 weight % based on the total of the organic layer comprising the compound (I). On the other hand, in the case of using the compound (I) as a material other than the host material, the weight ratio of the compound (I) is preferably 1 to 100 weight %, more preferably 25 to 100 weight %, particularly preferably 50 to 100 weight % based on the total of the organic layer comprising the compound (I).

Method for providing the organic layer comprising the compound (I) is not particularly limited, and the organic layer may be provided by a resistance heating vapor deposition method, an electron beam method, a sputtering method, a molecular stacking method, a coating method (a spin-coating method, a casting method, a dip-coating method, etc.), an ink-jet method, a printing method, a transferring method, etc. Among the methods, preferred are the resistance heating vapor deposition method and the coating method from the viewpoints of simplification of production processes and properties of the light-emitting device. Thickness of the organic layer comprising the compound (I) is also not particularly limited. In general, the thickness is preferably 1 to 200 nm, more preferably 5 to 100 nm.

In the organic layer comprising the compound (I), the compound (I) is preferably dispersed in a polymer. Examples of the polymer include poly(vinyl chloride), polycarbonates, polystyrene, poly(methyl methacrylate), polyesters, polysulfones, poly(phenylene oxide), polybutadiene, poly(N-vinylcarbazole), hydrocarbon resins, ketone resins, phenoxy resins, polyamides, ethyl celluloses, poly(vinyl acetate), ABS resins, polyurethanes, melamine resins, unsaturated polyester resins, alkyd resins, epoxy resins, silicone resins, etc. Weight ratio of the polymer is preferably 10 to 90 weight %, more preferably 20 to 60 weight % based on the total of the organic layer comprising the compound (I).

It is preferred that the organic layer comprising the compound (I) further comprises a transition metal complex. It is particularly preferable that the compound (I) is used as the host compound and doped with the transition metal complex acting as a guest compound. It is preferred that $T_1$ level of the guest compound (the transition metal complex) is smaller than that of the host compound (the compound (I)), wherein "$T_1$ level" means an energy level at a lowest triplet excited state. Further, $T_1$ level of a compound contained in a layer such as a hole-transporting layer, an electron-transporting layer, a hole-blocking layer, etc. adjacent to the light-emitting layer is preferably larger than that of the guest compound contained in the light-emitting layer, more preferably larger than that of the host compound contained in the light-emitting layer. The transition metal complex used in the present invention may be such a compound that is described in: Masatoshi Watabe, Shigenobu Yano and Takao Ikariya, "Sakutai-Kagaku No Kiso, Werner Sakutai To Yuki Kinzoku Sakutai (Foundation of Coordination Chemistry, Werner Complex and Organic Metal Complex)" Kodansha Ltd. (1989); Akio Yamamoto, "Yukikinzoku-Kagaku, Kiso To Oyo (Metalorganic Chemistry, Foundation and Application)", Page 150 to 232, Shokabo Publishing Co., Ltd., (1982); etc. Weight ratio of the transition metal complex is preferably 0.1 to 10 weight %, more preferably 0.5 to 3 weight % based on the total of the organic layer comprising the compound (I).

A central metal atom of the transition metal complex is not particularly limited. The transition metal complex may comprise one transition metal atom or a plurality of transition metal atoms, thus, the transition metal complex may be a so-called multi-nuclear complex. In the multi-nuclear complex, a plurality of transition metal atoms may be the same or different atoms. Number of carbon atoms in the transition metal complex is preferably 5 to 100, more preferably 10 to 60, particularly preferably 12 to 40.

The transition metal complex may comprise one or more kind of ligand. The ligand is not particularly limited and may be such that is described in: H. Yersin, "Photochemistry and Photophysics of Coordination Compounds", Springer-Verlag, Inc. (1987); Akio Yamamoto, "Yukikinzoku-Kagaku, Kiso To Oyo (Metalorganic Chemistry, Foundation and Application)", Shokabo Publishing Co., Ltd., (1982); etc. Examples of the ligand include: halogen ligands such as a chlorine ligand; nitrogen-containing heterocyclic ligands such as bipyridyl ligands, phenanthroline ligands and phenylpyridine ligands; diketone ligands such as an acetylacetone ligand; phosphorus ligands such as triphenylphosphine ligands, tributylphosphine ligands and trimethyl phosphite ligands; isocyanide ligands such as t-butylisocyanide ligands; a carbon monoxide ligand; etc.

The transition metal complex may be a neutral complex or an ionic complex containing a counter ion. The counter ion is not particularly limited and may be such that is described in Akio Yamamoto, "Yukikinzoku-Kagaku, Kiso To Oyo (Metalorganic Chemistry, Foundation and Application)", Shokabo Publishing Co., Ltd., (1982), etc. Further, the transition metal complex may be a low molecular weight compound, or an oligomer or a polymer having repeating units. In the case where the transition metal complex is the oligomer or the polymer, its weight-average molecular weight determined by polystyrene standard is preferably 1,000 to 5,000,000, more preferably 2,000 to 1,000,000, particularly preferably 3,000 to 100,000.

The transition metal complex is preferably an ortho-metallation complex, more preferably an ortho-metallation iridium complex. The ortho-metallation complex used in this invention may be such as described in: Akio Yamamoto, "Yukikinzoku-Kagaku, Kiso To Oyo (Metalorganic Chemistry, Foundation and Application)", Page 150 and 232, Shokabo Publishing Co., Ltd., (1982); H. Yersin, "Photochemistry and Photophysics of Coordination Compounds", Page 71 to 77 and 135 to 146, Springer-Verlag, Inc. (1987); etc.

A central metal atom of the ortho-metallation complex may be selected from transition metals. The central metal is preferably rhodium, platinum, gold, iridium, ruthenium or palladium, particularly preferably iridium. The iridium atom in the ortho-metallation complex is preferably trivalent, although valence of the central metal atom is not particularly limited. Number of carbon atoms of the ortho-metallation complex is preferably 5 to 100, more preferably 10 to 60, particularly preferably 12 to 40.

The ortho-metallation complex may comprise one or more kind of ligand, and preferably comprises 1 to 3 kind of ligand, more preferably comprises 1 or 2 kind of ligand, particularly preferably comprises 1 kind of ligand.

Although ligand of the ortho-metallation complex is not particularly limited, the ortho-metallation complex generally comprises a particular ligand. Examples of the particular ligand include: aryl-substituted, nitrogen-containing heterocyclic derivatives; heteroaryl-substituted, nitrogen-containing heterocyclic derivatives; 7,8-benzoquinoline derivatives; phosphinoaryl derivatives; phosphinoheteroaryl derivatives; phosphinoxyaryl derivatives; phosphinoxyheteroaryl derivatives; aminomethylaryl derivatives; aminomethylheteroaryl derivatives; etc. In the aryl-substituted, nitrogen-containing heterocyclic derivatives and the heteroaryl-substituted, nitrogen-containing heterocyclic derivatives, nitrogen-containing heterocycle may be a pyridine ring, a pyrimidine ring, a pyrazine ring, a pyridazine ring, a quinoline ring, an isoquinoline ring, a quinoxaline ring, a phthalazine ring, a quinazoline ring, a naphthylizine ring, a cinnoline ring, a perimidine ring, a phenanthroline ring, a pyrrole ring, an imidazole ring, a pyrazole ring, an oxazole ring, an oxadiazole ring, a triazole ring, a thiadiazole ring, a benzimidazole ring, a benzoxazole ring, a benzthiazole ring, a phenanthridine ring, etc. In the aryl-substituted, nitrogen-containing heterocyclic derivatives, the aryl group generally bonds to a carbon atom adjacent to the nitrogen atom in the nitrogen-containing heterocycle. The aryl group may be a phenyl group, a naphthyl group, an anthracenyl group, a pyrenyl group, etc. Further, in the heteroaryl-substituted, nitrogen-containing heterocyclic derivatives, the heteroaryl group generally bonds to a carbon atom adjacent to the nitrogen atom in the nitrogen-containing heterocycle. The heteroaryl group may be a group containing the above-exemplified nitrogen-containing heterocycle, a thiophenyl group, a furyl group, etc.

The particular ligand forming the ortho-metallation complex is preferably an aryl-substituted, nitrogen-containing heterocyclic derivative, a heteroaryl-substituted, nitrogen-containing heterocyclic derivative or a 7,8-benzoquinoline derivative, more preferably a phenylpyridine derivative, a thiophenylpyridine derivative or a 7,8-benzoquinoline derivative, particularly preferably a thiophenylpyridine derivative or a 7,8-benzoquinoline derivative.

In addition to the particular ligand, the ortho-metallation complex may comprise other ligand, which is not particularly limited and may be such that is described in: H. Yersin, "Photochemistry and Photophysics of Coordination Compounds", Springer-Verlag, Inc. (1987); Akio Yamamoto, "Yukikinzoku-Kagaku, Kiso To Oyo (Metalorganic Chemistry, Foundation and Application)", Shokabo Publishing Co., Ltd., (1982); etc. The other ligand is preferably a halogen ligand such as a chlorine ligand, a nitrogen-containing heterocyclic ligand such as a bipyridyl ligand and a phenanthroline ligand, or a diketone ligand, more preferably a chlorine ligand or a bipyridyl ligand.

The ortho-metallation complex used in the present invention is preferably a complex containing a moiety represented by the following formula (K-I) or a tautomer thereof.

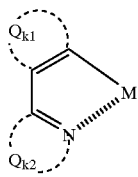

Formula (K-I)

In the formula (K-I), M represents a transition metal atom. M is preferably rhodium, platinum, gold, iridium, ruthenium or palladium, more preferably rhodium, platinum or iridium, particularly preferably platinum or iridium, the most preferably iridium.

In the formula (K-I), $Q_{k1}$ represents an atomic group forming a 5- or 6-membered aromatic ring. The 5- or 6-membered aromatic ring formed by $Q_{k1}$ may be an aromatic hydrocarbon ring or an aromatic heterocycle, and examples thereof include a benzene ring, a naphthalene ring, an anthracene ring, a pyrene ring, a pyridine ring, a quinoline ring, an isoquinoline ring, a pyridazine ring, a pyrimidine ring, a pyrazine ring, a thiophene ring, a furan ring, a pyrrole ring, a pyrazole ring, an imidazole ring, a thiazole ring, an oxazole ring, a thiadiazole ring, an oxadiazole ring, a triazole ring, a quinoxaline ring, a phthalazine ring, a naphthylizine ring, a cinnoline ring, a perimidine ring, a phenanthroline ring, a benzthiazole ring, a benzoxazole ring, a benzimidazole ring, a phenanthridine ring, etc. Of these, preferred are a benzene ring, a naphthalene ring, a pyridine ring, a quinoline ring, an isoquinoline ring, a thiophene ring and a furan ring, more preferred are a benzene ring, a naphthalene ring, a pyridine ring, a quinoline ring, an isoquinoline ring and a thiophene ring, particularly preferred are a benzene ring, a naphthalene ring and a thiophene ring.

In the formula (K-I), $Q_{k2}$ represents an atomic group forming a 5- or 6-membered aromatic azole ring. Examples of the 5- or 6-membered aromatic azole ring formed by $Q_{k2}$ include a pyridine ring, a quinoline ring, an isoquinoline ring, a pyridazine ring, a pyrimidine ring, a pyrazine ring, a pyrazole ring, an imidazole ring, a thiazole ring, an oxazole ring, a thiadiazole ring, an oxadiazole ring, a triazole ring, a quinoxaline ring, a phthalazine ring, a naphthylizine ring, a cinnoline ring, a perimidine ring, a phenanthroline ring, a benzthiazole ring, a benzoxazole ring, a benzimidazole ring, a phenanthridine ring, etc. Of these, preferred are a pyridine ring, a quinoline ring, an isoquinoline ring, a pyrazole ring and a pyridazine ring, more preferred are a pyridine ring, a quinoline ring, an isoquinoline ring and a pyrazole ring, particularly preferred are a pyridine ring, a quinoline ring and an isoquinoline ring.

The rings formed by $Q_{k1}$ and $Q_{k2}$ may have a substituent with examples being the same as those of $R_{11}$. The substituent on the $Q_{k1}$ and $Q_{k2}$ is preferably an alkyl group, an alkenyl group, an alkynyl group, an aryl group, an amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a halogen atom, a cyano group or a heterocyclic group, more preferably an alkyl group, an aryl group, an alkoxy group, an aryloxy group, an alkylthio group, an arylthio group, a halogen atom, a cyano group or a heterocyclic group, particularly preferably an alkyl group, an aryl group, an alkoxy group, an aryloxy group, a halogen atom or a cyano group. A plurality of the substituents may bond together to form a ring on the $Q_{k1}$ and $Q_{k2}$.

The ortho-metallation complex containing the moiety represented by the formula (K-I) and the tautomer thereof may comprise one or more transition metal atom, thus, may be a so-called multi-nuclear complex. In the multi-nuclear complex, a plurality of transition metal atoms may be the same or different atoms.

The ortho-metallation complex used in the present invention is more preferably a complex represented by the following formula (K-II) or a tautomer thereof.

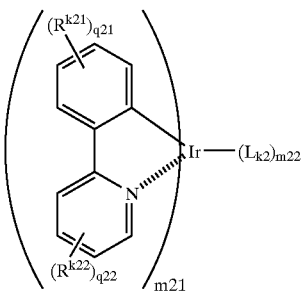

Formula (K-II)

In the formula (K-II), $R^{k21}$ and $R^{k22}$ represent a substituent with examples being the same as those of $R_{11}$, respectively. $R^{k21}$ and $R^{k22}$ may be further substituted and may bond together to form a condensed ring. It is preferable that $R^{k21}$ and $R^{k22}$ are an alkyl group, an aryl group, a heterocyclic group, an alkoxy group, an aryloxy group or a halogen atom, respectively, or bond together to form a condensed ring. It is more preferable that $R^{k21}$ and $R^{k22}$ are an alkyl group, an aryl group or a fluorine atom, respectively, or bond together to form a condensed aromatic ring.

In the formula (K-II), q21 and q22 are an integer of 0 to 4, preferably an integer of 0 to 2, respectively. It is particularly preferred that the sum of q21 and q22 is 0, 1 or 2. When q21 is 2 or more, a plurality of $R^{k21}$'s may be the same or different substituents. When q22 is 2 or more, a plurality of $R^{k22}$'s may be the same or different substituents.

In the formula (K-II), $L_{k2}$ represents a ligand. Examples of the ligand of $L_{k2}$ include those of the above-mentioned particular ligand and other ligand for the ortho-metallation complex. $L_{k2}$ is preferably the above-mentioned particular ligand, a nitrogen-containing heterocyclic ligand, a diketone ligand, a halogen ligand, a phosphorus ligand, an isonitrile ligand or a carbon monoxide ligand, more preferably the above-mentioned particular ligand, a diketone ligand, a bipyridyl ligand, a phosphorus ligand or an isonitrile ligand.

In the formula (K-II), m21 is an integer of 1 to 3, preferably 2 or 3, more preferably 3. m22 is an integer of 0 to 5, preferably an integer of 0 to 2, more preferably 0 or 1. m21 and m22 are preferably selected in combination with each other such that the complex represented by the formula (K-II) is a neutral complex.

The ortho-metallation complex is preferably a low molecular weight compound though it may be an oligomer or a polymer having a plurality of repeating units. The weight-average molecular weight of the oligomer and polymer determined by polystyrene standard is preferably 1,000 to 5,000,000, more preferably 2,000 to 1,000,000, particularly preferably 3,000 to 100,000. Specific examples of the ortho-metallation complex used in the present invention will be illustrated below without intention of restricting the scope of the present invention defined by the claims attached hereto.

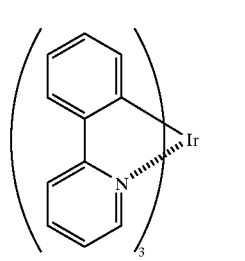

K-1

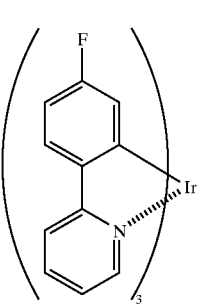

K-2

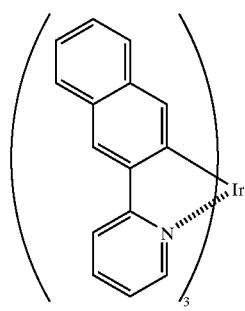

K-3

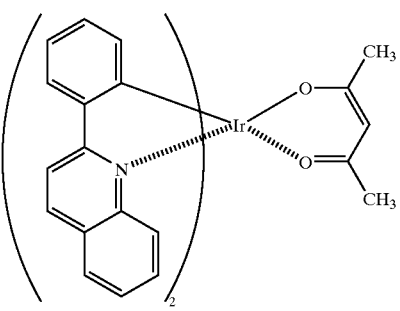

K-4

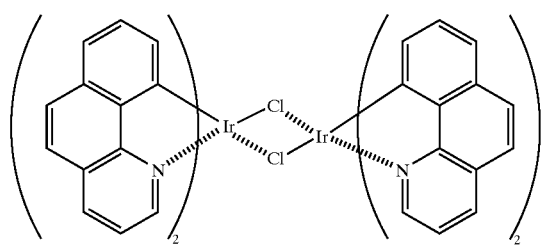

K-5

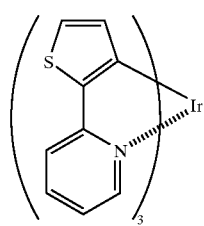

K-6

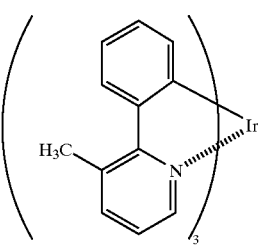

K-7

-continued
K-8
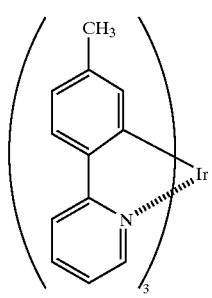
K-9
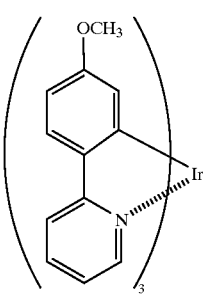
K-10
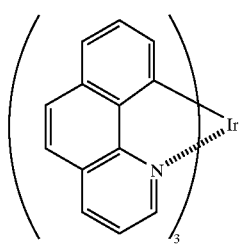
K-11
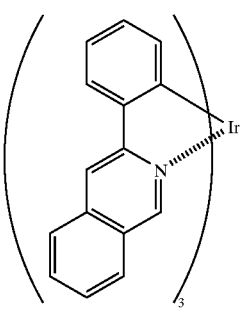
K-12
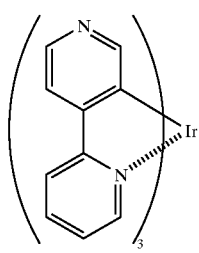
K-13
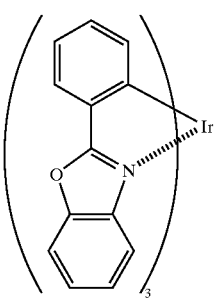
K-14
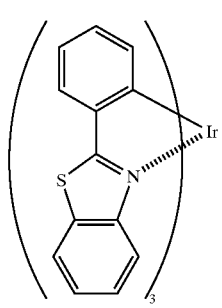
K-15
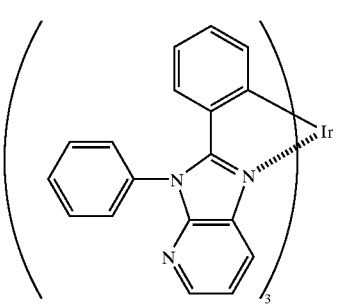
K-16
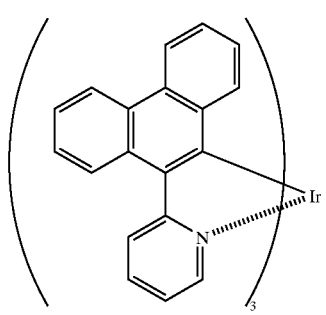
K-17
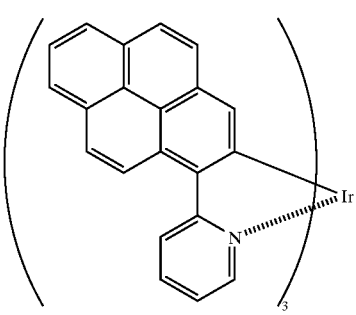

-continued
K-18
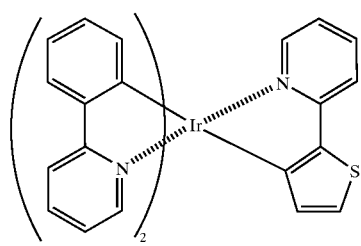
K-19
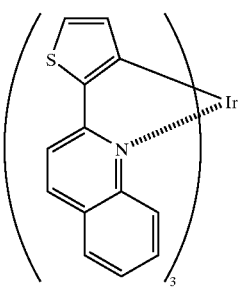
K-20
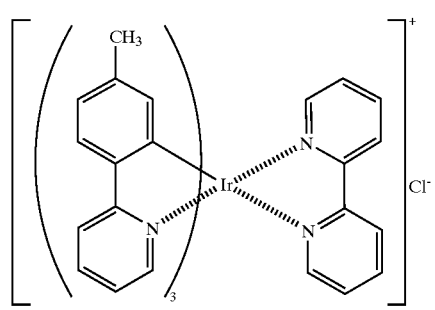
K-21
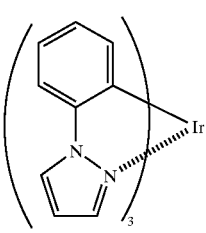
K-22
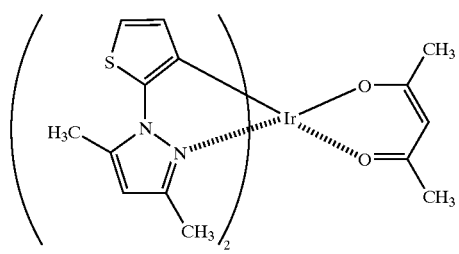
K-23
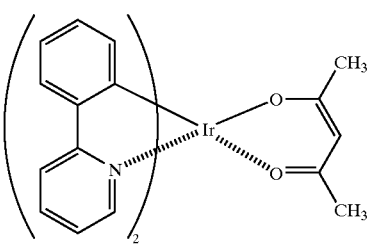
K-24
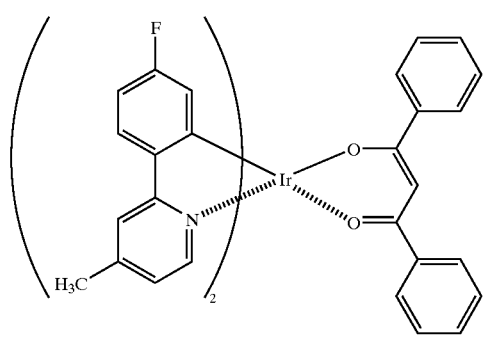
K-25
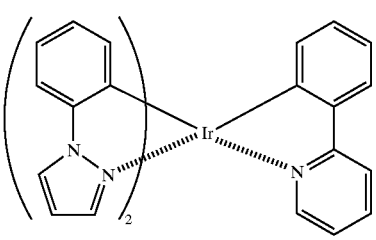
K-26
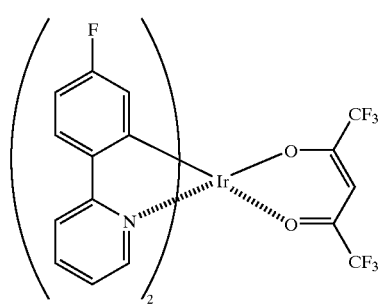
K-27
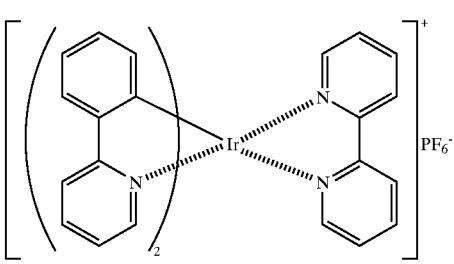

-continued
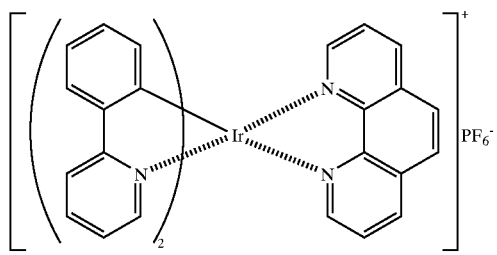
K-28
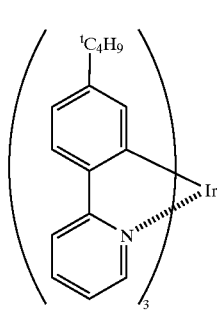
K-29
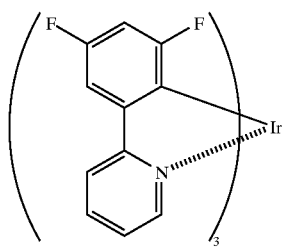
K-30
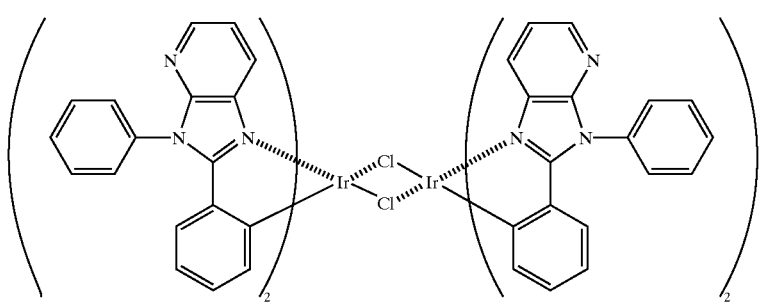
E-31
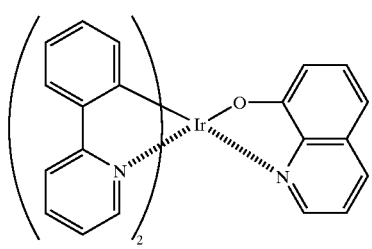
K-32
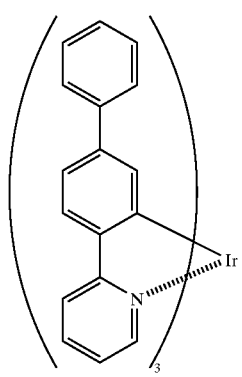
K-33
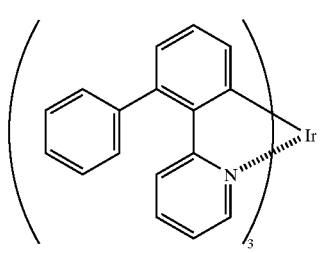
K-34
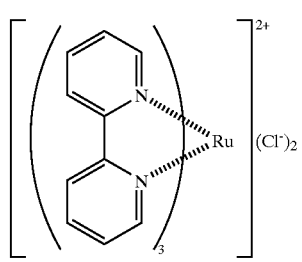
K-35

K-36 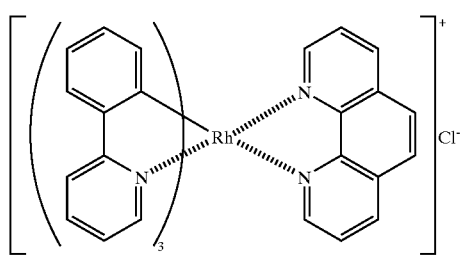
K-37 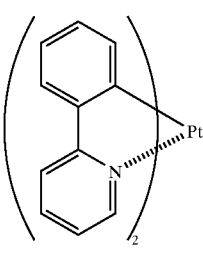
K-38 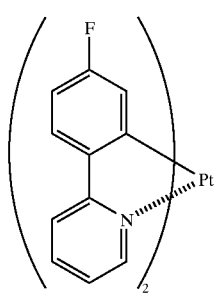
K-39 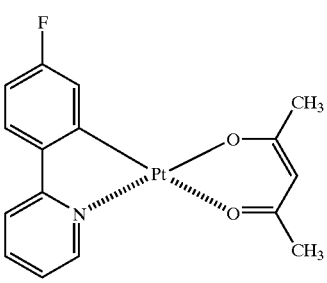
K-40 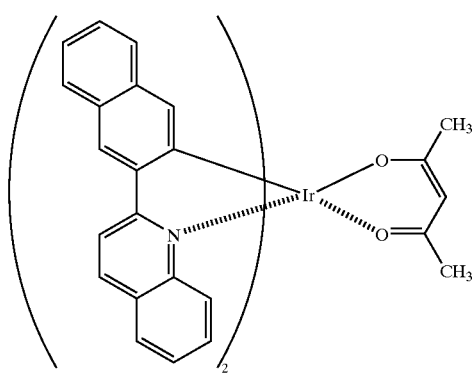
K-41 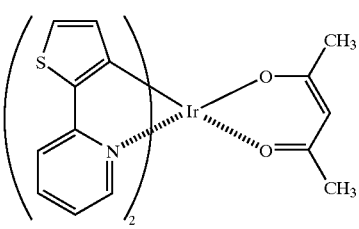
K-42 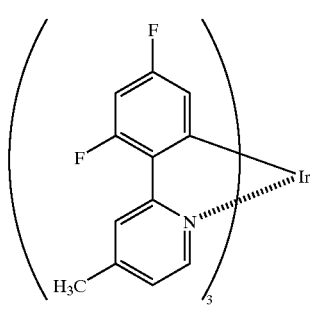
K-43 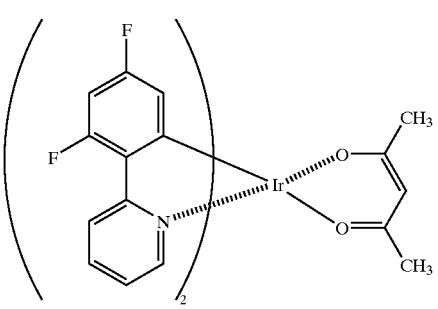
K-44 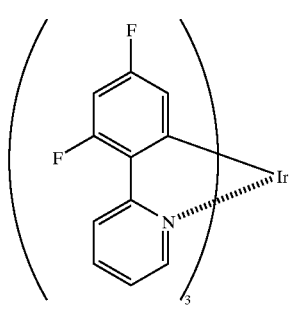
K-45 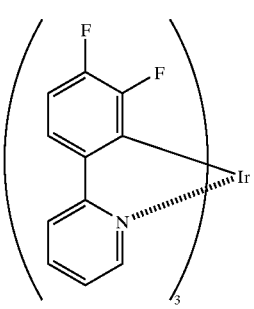

-continued

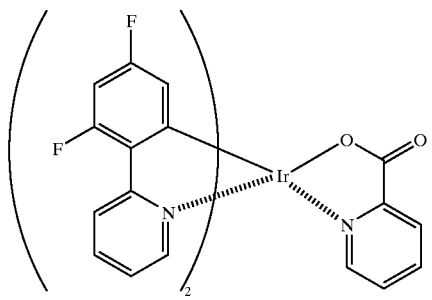
K-46

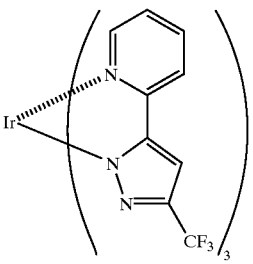
K-47

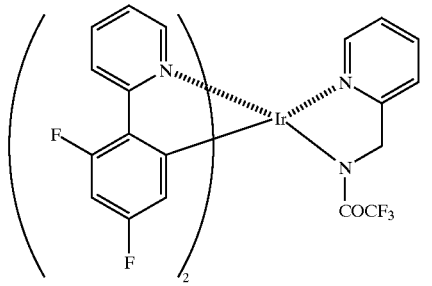
K-48

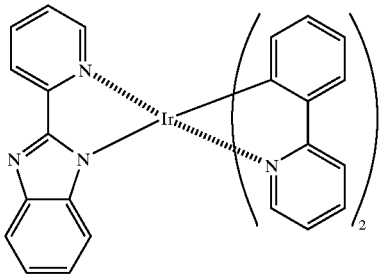
K-49

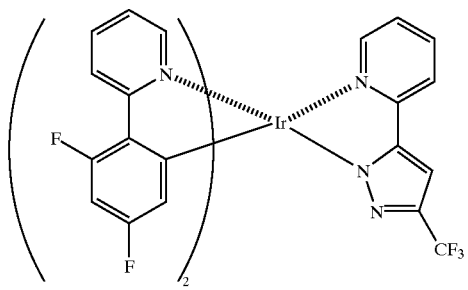
K-50

The ortho-metallation complex used in the present invention may be synthesized by a known method described in: Inorg. Chem., 1991, Vol. 30, Page 1685; Inorg. Chem., 1988, Vol. 27, Page 3464; Inorg. Chem., 1994, Vol. 33, Page 545; Inorg. Chim. Acta, 1991, Vol. 181, Page 245; J. Organomet. Chem., 1987, Vol. 335, Page 293; J. Am. Chem. Soc., 1985, Vol. 107, Page 1431; etc.

The organic layer comprising the compound (I) may further comprise a charge-transporting material other than the compound (I), etc. in addition to the above-mentioned polymer and transition metal complex.

The light-emitting device of the present invention comprises the light-emitting layer, and may further comprise a hole-injecting layer, a hole-transporting layer, an electron-injecting layer, an electron-transporting layer, a protective layer, etc. These layers may have a plurality of functions. The compound (I) may be contained in any of the layers. The compound (I) is preferably used for the electron-injecting layer, the electron-transporting layer and/or the light-emitting layer. Each component of the light-emitting device according to the present invention will be described in detail below.

(A) Positive Electrode

The positive electrode acts to supply holes to the hole-injecting layer, the hole-transporting layer, the light-emitting layer, etc. The positive electrode is generally made of a metal, an alloy, a metal oxide, an electrically conductive compound, a mixture thereof, etc., preferably made of a material having a work function of 4.0 eV or more. Examples of a material for the positive electrode include: metals such as gold, silver, chromium and nickel; electrically conductive metal oxides such as tin oxide, zinc oxide, indium oxide and ITO (Indium Tin Oxide); mixtures and laminations of the metal and the electrically conductive metal oxide; electrically conductive inorganic compounds such as copper iodide and copper sulfide; electrically conductive organic compounds such as polyaniline, polythiophene and polypyrrole; laminations of the electrically conductive organic compound and ITO; etc. Among the materials, preferred are the electrically conductive metal oxides, particularly preferred is ITO from the viewpoints of productivity, electroconductivity, transparency, etc.

Method for providing the positive electrode may be selected depending on the material used therefor. For example, the positive electrode made of ITO may be formed by an electron beam method, a sputtering method, a resistance heating vapor deposition method, a chemical reaction method such as a sol-gel method, a coating method using a dispersion containing indium tin oxide, etc. The positive electrode may be subjected to a washing treatment, etc., to lower the driving voltage, or to increase the light-emitting efficiency of the light-emitting device. For example, in the case of the positive electrode made of ITO, UV-ozone treatment and plasma treatment are effective. Sheet resistance of the positive electrode is preferably a few hundred Ω/square or less. Although thickness of the positive electrode may be appropriately selected depending on the material used therefor, generally, the thickness is preferably 10 nm to 5 μm, more preferably 50 nm to 1 μm, particularly preferably 100 to 500 nm.

The positive electrode is generally disposed on a substrate made of a soda lime glass, a non-alkali glass, a transparent resin, etc. The glass substrate is preferably made of the non-alkali glass to reduce ion elution. In the case of using the soda lime glass, it is preferred that the substrate is coated with silica, etc. beforehand. Thickness of the substrate is not particularly limited if only it has sufficient strength. In the case of the glass substrate, the thickness is generally 0.2 mm or more, preferably 0.7 mm or more.

(B) Negative Electrode

The negative electrode acts to supply electrons to the electron-injecting layer, the electron-transporting layer, the light-emitting layer, etc. Material for the negative electrode may be selected from metals, alloys, metal halides, metal oxides, electrically conductive compounds, mixtures thereof, etc. correspondingly to ionization potential, stability, adhesion property with a layer adjacent to the negative electrode such as the light-emitting layer, etc. Examples of the material for the negative electrode include: alkali metals such as Li, Na, K and Cs, and fluorides and oxides thereof; alkaline earth metals such as Mg and Ca, and fluorides and oxides thereof; gold; silver; lead; aluminum; alloys and mixtures of sodium and potassium; alloys and mixtures of lithium and aluminum; alloys and mixtures of magnesium and silver; rare earth metals such as indium and ytterbium; mixtures thereof; etc. The negative electrode is preferably made of a material having a work function of 4.0 eV or less, more preferably made of aluminum, an alloy or a mixture of lithium and aluminum, or an alloy and a mixture of magnesium and silver.

The negative electrode may have a single-layer structure or a multi-layer structure. Preferred multi-layer structure is aluminum/lithium fluoride, aluminum/lithium oxide, etc. The negative electrode may be provided by an electron beam method, a sputtering method, a resistance heating vapor deposition method, a coating method, etc. A plurality of materials may be simultaneously deposited. The negative electrode of an alloy may be formed by simultaneously depositing a plurality of metals, or by depositing an alloy prepared beforehand. Sheet resistance of the negative electrode is preferably a few hundred Ω/square or less. Although thickness of the negative electrode may be appropriately selected depending on the material used therefor, generally, the thickness is preferably 10 nm to 5 μm, more preferably 50 nm to 1 μm, particularly preferably 100 nm to 1 μm.

(C) Hole-Injecting Layer and Hole-Transporting Layer

The hole-injecting material and the hole-transporting material used for the hole-injecting layer and the hole-transporting layer are not particularly limited if they have any function of: injecting the holes provided from the positive electrode into the light-emitting layer; transporting the holes to the light-emitting layer; and blocking the electrons provided from the negative electrode. Examples of the hole-injecting material and the hole-transporting material include carbazole, triazole, oxazole, oxadiazole, imidazole, polyarylalkanes, pyrazoline, pyrazolone, phenylenediamine, arylamines, amino-substituted chalcone, styrylanthracene, fluorenone, hydrazone, stilbene, silazane, aromatic tertiary amine compounds, styrylamine compounds, aromatic dimethylidyne compounds, porphyrin compounds, polysilane compounds, poly(N-vinylcarbazole), aniline copolymers, electrically conductive polymers and oligomers such as oligothiophenes and polythiophenes, organic silane compounds, derivatives thereof, carbon, etc.

Each of the hole-injecting layer and the hole-transporting layer may have a structure of single-layer made of one or more materials, or multi-layers made of the same material or different materials. The hole-injecting layer and the hole-transporting layer may be formed by a vacuum deposition method, an LB method, a coating method using a solution or a dispersion containing the above material such as a spin-coating method, a casting method and a dip-coating method, an ink-jet method, a printing method, a transferring method, etc.

The solution and the dispersion used in the coating method may contain a resin. Examples of the resin include poly(vinyl chloride), polycarbonates, polystyrene, poly (methyl methacrylate), poly(butyl methacrylate), polyesters, polysulfones, poly(phenylene oxide), polybutadiene, poly (N-vinylcarbazole), hydrocarbon resins, ketone resins, phenoxy resins, polyamides, ethyl celluloses, poly(vinyl acetate), ABS resins, polyurethanes, melamine resins, unsaturated polyester resins, alkyd resins, epoxy resins, silicone resins, etc. Although the thickness of each of the hole-injecting layer and the hole-transporting layer is not particularly limited, generally, the thickness is preferably 1 nm to 5 μm, more preferably 5 nm to 1 μm, particularly preferably 10 to 500 nm.

(D) Light-Emitting Layer

In the light-emitting layer, holes injected from the positive electrode, the hole-injecting layer or the hole-transporting layer and electrons injected from the negative electrode, the electron-injecting layer or the electron-transporting layer are recombined to emit light when electric field is applied to the light-emitting device. A light-emitting material for the light-emitting layer are not particularly limited if only they have functions of: receiving the holes provided from the positive electrode, etc.; receiving the electrons provided from the negative electrode, etc.; transporting the charges; and providing the occasion where the holes and the electrons are recombined to emit light when electric field is applied to the light-emitting device. The light-emitting material may be such that utilizes singlet exciton, triplet exciton or both thereof for light emission, and examples thereof include: benzoxazole; benzoimidazole; benzothiazole; styrylbenzene; polyphenyl; diphenylbutadiene; tetraphenylbutadiene; naphthalimido; coumarin; perylene; perynone; oxadiazole; aldazine; pyralidine; cyclopentadiene; bis(styryl) anthracene; quinacridon; pyrrolopyridine; thiadiazolopyridine; cyclopentadiene; styrylamine; aromatic dimethylidine compounds; metal complexes such as 8-quinolinol metal complexes, rare-earth metal complexes and ortho-metallation complexes (tris(2-phenylpyridine)-iridium (III), etc.); high molecular weight light-emitting material such as polythiophene, polyphenylene, polyphenylenevinylene and polyfluorene; organic silane compounds; derivatives thereof; the compound (I) having a purine skeleton; etc.

The light-emitting layer may be formed by: a resistance heating vapor deposition method; an electron beam method; a sputtering method; a molecular stacking method; a coating method such as a spin-coating method, a casting method and a dip-coating method; an ink-jet method; a printing method; an LB method; a transferring method; etc. Among the methods, the resistance heating vapor deposition method and the coating method are preferred. Although thickness of the light-emitting layer is not particularly limited, generally, the thickness is preferably 1 nm to 5 μm, more preferably 5 nm to 1 μm, particularly preferably 10 to 500 nm.

(E) Electron-Injecting Layer and Electron-Transporting Layer

The electron-injecting material and the electron-transporting material used for the electron-injecting layer and the electron-transporting layer are not particularly limited if they have any function of: injecting the electrons provided from the negative electrode into the light-emitting layer; transporting the electrons to the light-emitting layer; and blocking the holes provided from the positive electrode. Although the electron-injecting layer and/or the electron-transporting layer is preferably made of the compound (I), other material may be used therefor. Examples of the other material include: triazole; oxazole; oxadiazole; fluorenone; anthraquinodimethane; anthrone; diphenylquinone; thiopyran dioxide; carbodimide; fluorenylidenemethane; distyrylpyrazine; anhydrides derived from a tetracarboxylic acid having such a ring as a naphthalene ring and a perylene ring; phthalocyanine; metal complexes such as 8-quinolinol metal complexes, metallophthalocyanines, and metal complexes containing a benzoxazole ligand or a benzothiazole ligand; derivatives thereof; etc.

Each of the electron-injecting layer and the electron-transporting layer may have a structure of single-layer made of one or more materials, or multi-layers made of the same material or different materials. The electron-injecting layer and the electron-transporting layer may be formed by a vacuum deposition method, an LB method, an ink-jet method, a printing method, a transferring method, a coating method using a solution or a dispersion containing the above material such as a spin-coating method, a casting method and a dip-coating method, etc. The solution and the dispersion used in the coating method may contain a resin. Examples of the resin may be the same as those for the hole-injecting layer and the hole-transporting layer. Although thickness of each of the electron-injecting layer and the electron-transporting layer is not particularly limited, generally, the thickness is preferably 1 nm to 5 µm, more preferably 5 nm to 1 µm, particularly preferably 10 to 500 nm.

(F) Protective Layer

The protective layer acts to shield the light-emitting device from penetration of moisture, oxygen, etc. that promotes deterioration of the device. Examples of a material for the protective layer include: metals such as In, Sn, Pb, Au, Cu, Ag, Al, Ti and Ni; metal oxides such as MgO, SiO, $SiO_2$, $Al_2O_3$, GeO, NiO, CaO, BaO, $Fe_2O_3$, $Y_2O_3$ and $TiO_2$; metal fluorides such as $MgF_2$, LiF, $AlF_3$ and $CaF_2$; polyethylene; polypropylene; poly(methylmethacrylate); polyimides; polyureas; polytetrafluoroethylene; polychlorotrifluoroethylene; polydichlorodifluoroethylene; copolymers of chlorotrifluoroethylene and dichlorodifluoroethylene; copolymers of tetrafluoroethylene and at least one comonomer; fluorine-containing copolymers having a cyclic structure in the main chain; a moisture-absorbing substance having a water absorption of 1% or more; a moisture-resistant substance having a water absorption of 0.1% or less; etc.

The protective layer may be formed by a vacuum deposition method, a sputtering method, an activated sputtering method, a molecular beam epitaxy method (MBE method), a cluster ion beam method, an ion-plating method, a plasma polymerization method, a high frequency excitation ion-plating method, a plasma CVD method, a laser CVD method, a thermal CVD method, a gas source CVD method, a coating method, an ink-jet method, a printing method, a transferring method, etc.

EXAMPLES

The present invention will be explained in further detail by the following Examples without intention of restricting the scope of the present invention defined by the claims attached hereto.

Synthesis Example 1

Synthesis of Compound (E-2)

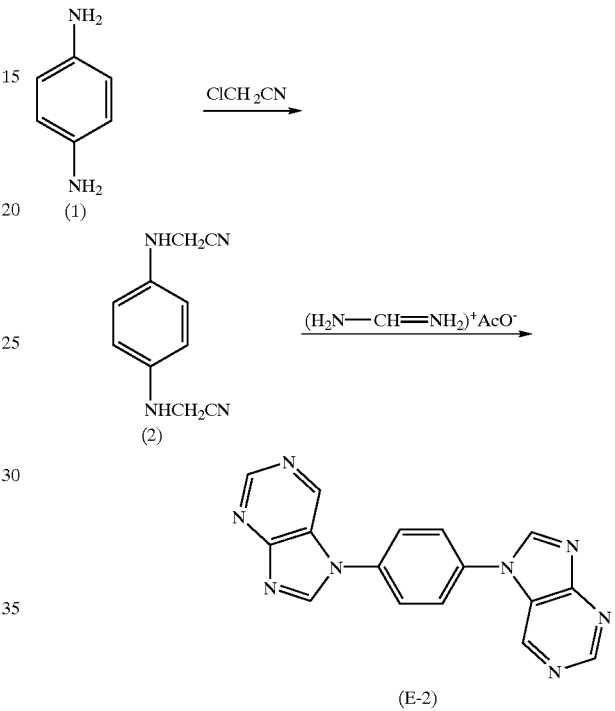

21.6 g of Compound (1), 67.2 g of sodium hydrogen carbonate and 150 ml of N,N-dimethylacetamide were put in a three-necked flask, and 27.8 ml of chloroacetonitrile was added thereto dropwise over 10 minutes while stirring at the inner temperature of 50° C. This was stirred for 3 hours at the inner temperature of 50° C., and further stirred for 2 hours at the inner temperature of 80° C. The resultant mixture was cooled to room temperature, and 500 ml of ethyl acetate and 500 ml of water were added thereto to extract the mixture. Thus-obtained ethyl acetate phase was washed five times with a mixture of 50 ml of saturated sodium chloride solution and 400 ml of water, dried over anhydrous sodium sulfate, and concentrated by a rotating evaporator. Residue was added 70 ml of acetonitrile to and stirred in an ice bath to precipitate a crystal. Then, the crystal was separated by vacuum filtration and dried to prepare 27.4 g of Compound (2) (Yield: 74%). 18.6 g of Compound (2), 208 g of formamidine acetate and 400 ml of 1-methoxy-2-propanol were put in a three-necked flask and stirred for 6 hours under heat reflux. This was cooled to the room temperature to precipitate a crystal, and then, the crystal was separated by vacuum filtration. Thus-obtained crystal was stirred in ethanol under heat reflux, separated by vacuum filtration, and dried to prepare 27.0 g of Compound (E-2) (Yield: 86%).

Synthesis Example 2

Synthesis of Compound (E-8)

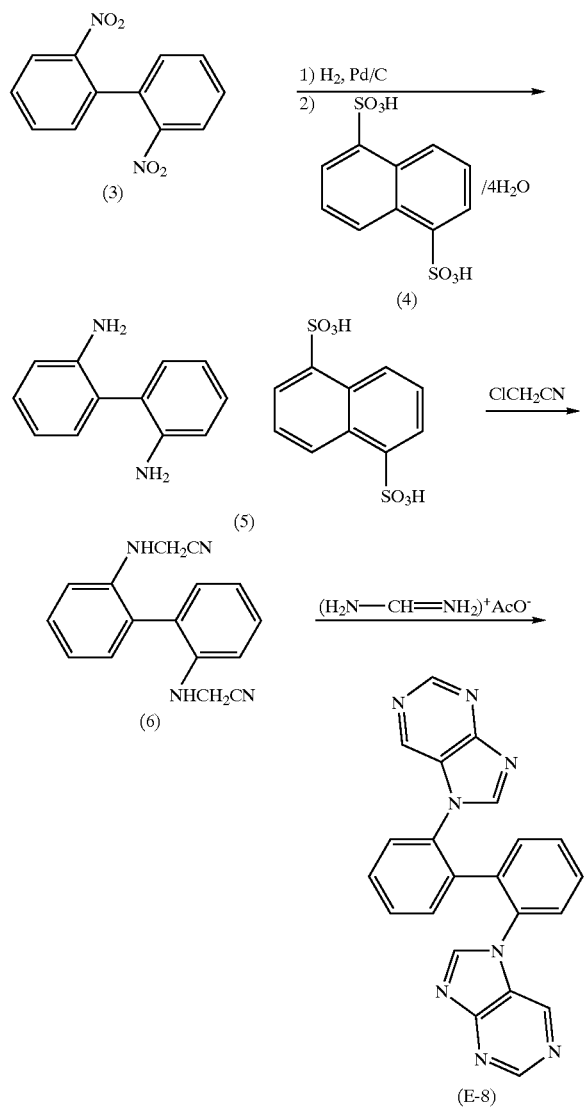

48.8 g of Compound (3), 5 g of wet Pd/C (10%) and 240 ml of methanol were put in an autoclave having an inner volume of 1000 ml and stirred at an inner temperature of 50° C. for 3 hours under a hydrogen pressure of 100 atmospheres while heating. After the resultant mixture was cooled to the room temperature, Pd/C was removed by filtration, and a solution containing 72 g of Compound (4) and 200 ml of methanol was added to the mixture to precipitate a crystal. Then, thus-obtained crystal was separated by vacuum filtration and dried under a reduced pressure to prepare 92.5 g of Compound (5) (Yield: 98%).

47.2 g of Compound (5), 67.2 g of sodium hydrogen carbonate and 150 ml of N,N-dimethylacetamide were put in a three-necked flask, and 13.9 ml of chloroacetonitrile was added thereto dropwise over 10 minutes while stirring at the inner temperature of 50° C. This was stirred for 3 hours at the inner temperature of 50° C., and further stirred for 2 hours at the inner temperature of 80° C. The resultant mixture was cooled to the room temperature, and 500 ml of ethyl acetate and 500 ml of water were added thereto to extract the mixture. Thus-obtained ethyl acetate phase was washed five times with a mixture of 50 ml of saturated sodium chloride solution and 400 ml of water, dried over anhydrous sodium sulfate, and concentrated by a rotating evaporator. Residue was purified by a silica gel column chromatography to prepare 21.5 g of Compound (6) (Yield: 82%).

26.2 g of Compound (6), 208 g of formamidine acetate and 400 ml of butanol were put in a three-necked flask and stirred for 8 hours under heat reflux. This was cooled to the room temperature to precipitate a crystal, and then, the crystal was separated by vacuum filtration. Thus-obtained crystal was stirred in ethanol under heat reflux, separated by vacuum filtration, and dried to prepare 29.3 g of Compound (E-8) (Yield: 75%).

Synthesis Example 3

Synthesis of Compound (E-41)

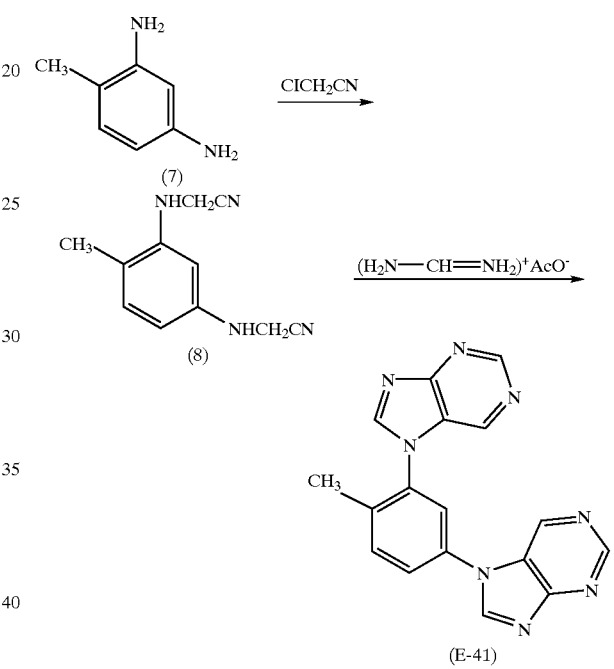

24.4 g of Compound (7), 67.2 g of sodium hydrogen carbonate and 100 ml of N,N-dimethylacetamide were put in a three-necked flask, and 27.8 ml of chloroacetonitrile was added thereto dropwise over 10 minutes while stirring at the inner temperature of 50° C. This was stirred for 3 hours at the inner temperature of 50° C., stirred for 2 hours at the inner temperature of 80° C., and further stirred for 3 hours at the inner temperature of 120° C. while heating. The resultant mixture was cooled to the room temperature, and 500 ml of ethyl acetate and 500 ml of water were added thereto to extract the mixture. Thus-obtained ethyl acetate phase was washed five times with a mixture of 50 ml of saturated sodium chloride solution and 400 ml of water, dried over anhydrous sodium sulfate, and concentrated by a rotating evaporator. Residue was purified by a silica gel column chromatography and by recrystallization from methanol to prepare 30.0 g of Compound (8) (Yield: 75%).

20.0 g of Compound (8), 208 g of formamidine acetate and 400 ml of 1-methoxy-2-propanol were put in a three-necked flask and stirred for 15 hours under heat reflux. This was cooled to the room temperature and concentrated by an evaporator, and then, residue was purified by a silica gel column chromatography to prepare 22.3 g of Compound (E-41) (Yield: 68%).

Synthesis Example 4

Synthesis of Compound (E-42)

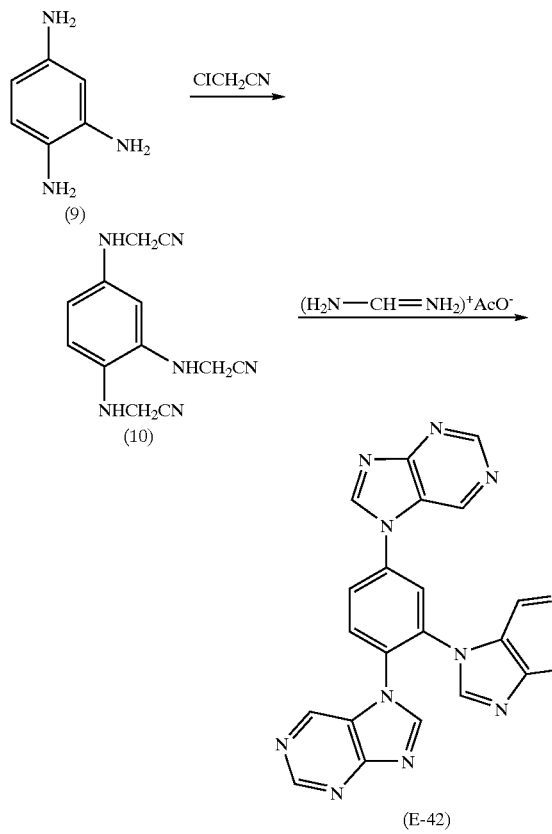

24.6 g of Compound (9), 100.8 g of sodium hydrogen carbonate and 100 ml of N,N-dimethylacetamide were put in a three-necked flask, and 41.8 ml of chloroacetonitrile was added thereto dropwise over 30 minutes while stirring at the inner temperature of 50° C. This was stirred for 3 hours at the inner temperature of 50° C., stirred for 2 hours at the inner temperature of 80° C., and further stirred for 3 hours at the inner temperature of 120° C. while heating. The resultant mixture was cooled to the room temperature, and 500 ml of ethyl acetate and 500 ml of water were added thereto to extract the mixture. Thus-obtained ethyl acetate phase was washed five times with a mixture of 50 ml of saturated sodium chloride solution and 400 ml of water, dried over anhydrous sodium sulfate, and concentrated by a rotating evaporator. Residue was purified by a silica gel column chromatography to prepare 30.3 g of Compound (10) (Yield: 63%).

24.0 g of Compound (10), 312 g of formamidine acetate and 400 ml of 1-methoxy-2-propanol were put in a three-necked flask and stirred for 15 hours under heat reflux. This was cooled to the room temperature and concentrated by an evaporator, and then, residue was purified by a silica gel column chromatography to prepare 25.9 g of Compound (E-42) (Yield: 60%).

Synthesis Example 5

Synthesis of Compound (E-51)

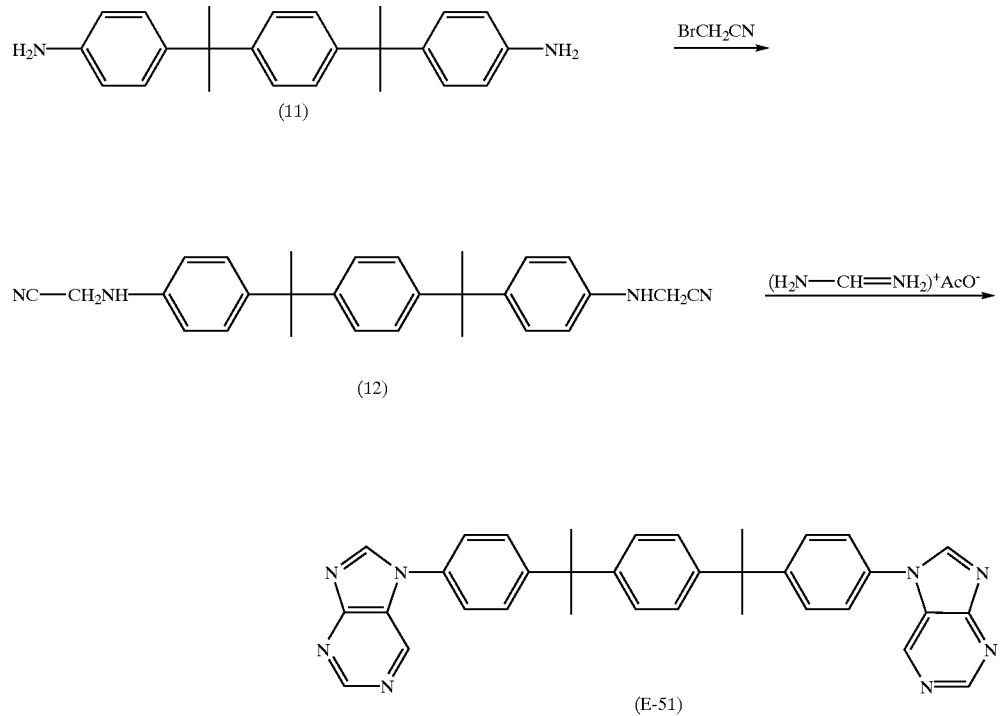

34.5 g of Compound (11), 34.0 g of sodium hydrogen carbonate and 100 ml of N,N-dimethylacetamide were put in a three-necked flask, and 15.2 ml of bromoacetonitrile was added thereto dropwise over 30 minutes while stirring at the inner temperature of 50° C. This was stirred for 3 hours at the inner temperature of 50° C., stirred for 2 hours at the inner temperature of 80° C., and further stirred for 2 hours at the inner temperature of 120° C. while heating. The resultant mixture was cooled to the room temperature, and 500 ml of ethyl acetate and 500 ml of water were added thereto to extract the mixture. Thus-obtained ethyl acetate phase was washed five times with a mixture of 50 ml of saturated sodium chloride solution and 400 ml of water, dried over anhydrous sodium sulfate, and concentrated by a rotating evaporator. Residue was added 150 ml of acetonitrile to and stirred in an ice bath to precipitate a crystal. Then, the crystal was separated by vacuum filtration to prepare 32.6 g of Compound (12) (Yield: 77%).

42.3 g of Compound (12), 208 g of formamidine acetate and 260 ml of 1-methoxy-2-propanol were put in a three-necked flask and stirred for 4 hours under heat reflux. This was cooled to the room temperature, added 1 L of chloroform to, and stirred to precipitate a crystal. The crystal was removed by filtration and the resultant filtrate was concentrated by a rotating evaporator. Then, residue was purified by a silica gel column chromatography to prepare 28.3 g of Compound (E-51) (Yield: 51%). Thus-obtained Compound (E-51) had a melting point of 263 to 267° C.

Synthesis Example 6

Synthesis of Compound (E-13)

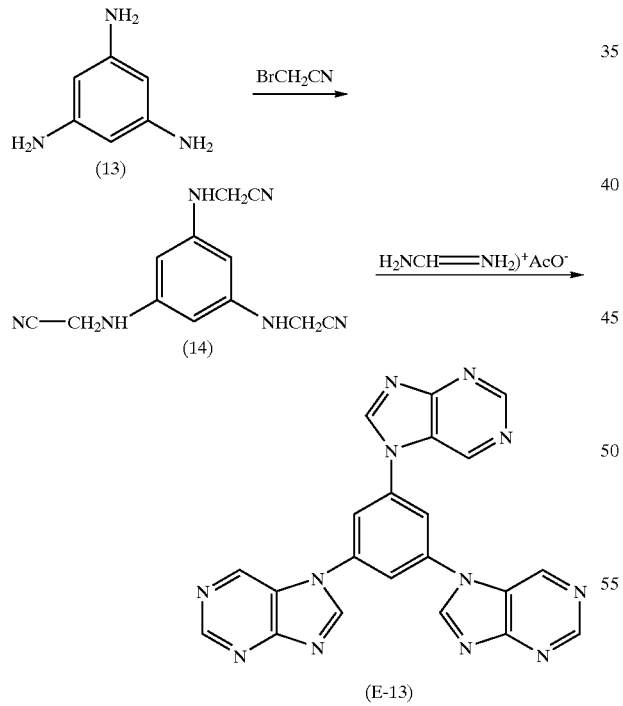

12.3 g of Compound (13), 50.4 g of sodium hydrogen carbonate and 100 ml of N,N-dimethylacetamide were put in a three-necked flask, and 22.8 ml of bromoacetonitrile was added thereto dropwise over 30 minutes while stirring at the inner temperature of 50° C. This was stirred for 3 hours at the inner temperature of 50° C., stirred for 2 hours at the inner temperature of 80° C., and further stirred for 12 hours at the inner temperature of 120° C. while heating. The resultant mixture was cooled to the room temperature and poured into an ice bath to precipitate a crystal. The crystal was separated by vacuum filtration and stirred in a mixed solvent of 100 ml of chloroform and 100 ml of methanol under heat reflux. After 3 hours of stirring, the resulting crystal was separated by vacuum filtration to prepare 8.6 g of Compound (14) (Yield: 36%).

8.6 g of Compound (14), 112 g of formamidine acetate and 150 ml of 1-methoxy-2-propanol were put in a three-necked flask and stirred for 24 hours under heat reflux. This was cooled to the room temperature and poured into an ice bath to precipitate a crystal. The crystal was separated by filtration, and then, 100 ml of chloroform and 100 ml of methanol was added to the crystal. The resultant mixture was stirred for 10 hours under heat reflux and subjected to vacuum filtration to prepare 2.33 g of Compound (E-13) (Yield: 15%). Thus-obtained Compound (E-13) had a melting point of 270° C. or more.

Synthesis Example 7

Synthesis of Compound (E-64)

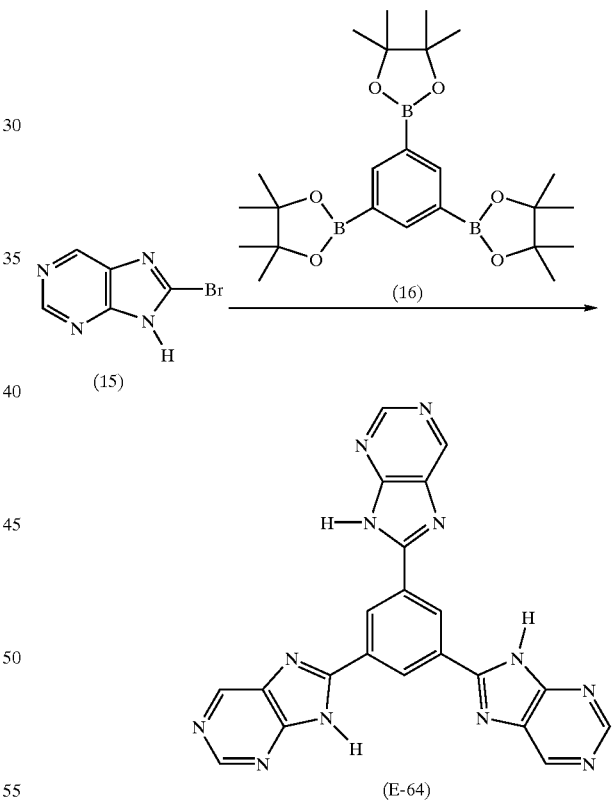

1.99 g of Compound (15), 1.37 g of Compound (16), 2.5 g of sodium hydrogen carbonate, 0.20 g of triphenylphosphine, 10 ml of toluene, 1.5 ml of ethanol and 5 ml of water were put in a three-necked flask, and thereto was further added 0.1 g of palladium (II) chloride-triphenylphosphine complex while stirring under reflux. The resultant mixture was stirred for 10 hours under heat reflux and added to acetonitrile to precipitate a crystal. The crystal was separated by vacuum filtration and washed with water. Then, the crystal was washed in a mixed solvent of 20 ml of methanol and 20 ml of chloroform while stirring under heat reflux, and subjected to vacuum filtration to prepare 0.32 g of Compound (E-64) (Yield: 25%). Thus-obtained Compound (E-64) had a melting point of 270° C. or more. Incidentally, Compound (15) was synthesized by a method described in Journal of Organic Chemistry, Vol. 27, Page 986 (1962).

Synthesis Example 8

Synthesis of Compound (E-57)

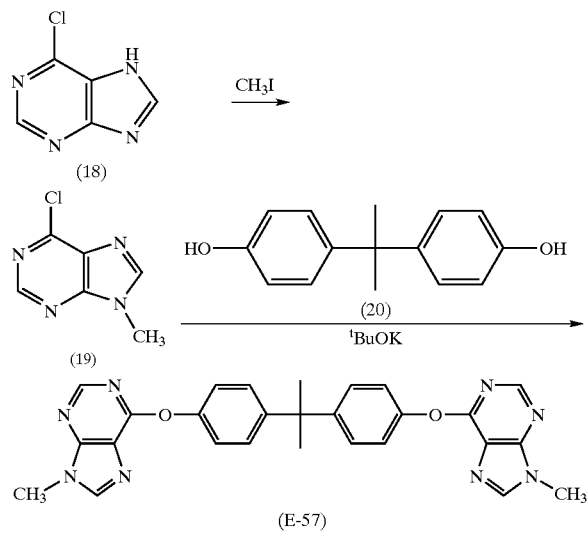

15.5 g of Compound (18) and 100 ml of tetrahydrofuran were put in a three-necked flask, and 16.5 ml of 1,8-diazabicyclo[5,4,0]-7-undecene was added thereto dropwise over 7 minutes while stirring at the inner temperature of 7 to 9° C. in an ice bath. After stirring the resultant mixture for 10 minutes, 8.1 ml of iodomethane was added thereto dropwise over 10 minutes at 8 to 10° C. This was stirred for 1 hour at 8 to 10° C., and further stirred for 5 hours while raising the temperature to the room temperature. The resulting mixture was concentrated by a rotating evaporator, and purified by a silica gel column chromatography to prepare 8.5 g of Compound (19) (Yield: 50%).

9.13 g of Compound (20) and 30 ml of N,N-dimethylacetamide were put in a three-necked flask, and 9.87 g of potassium-t-butoxide was added thereto while stirring at the room temperature. This was stirred for 20 minutes at the inner temperature of 100° C. and cooled to the room temperature. Then, 14.84 g of Compound (19) was added thereto while stirring and stirred at the room temperature for 2 hours, and this was further stirred at the inner temperature of 100° C. for 2 hours while heating. The resulting mixture was cooled to the room temperature and poured into an ice bath to precipitate a crystal. The crystal was separated by vacuum filtration, and then, a mixed solvent of 20 ml of chloroform and 30 ml of methanol was added to the crystal. The mixture was stirred for 1 hour under heat reflux, 20 ml of the mixed solvent was distilled off, and the resulting crystal was separated by vacuum filtration to prepare 11.7 g of Compound (E-57) (Yield: 59%). Thus-obtained Compound (E-57) had a melting point of 270° C. or more.

Example 1

A glass substrate having an ITO electrode was washed, and on the glass substrate were vacuum vapor-deposited copper phthalocyanine in 5 nm thickness, N,N'-bis(1-naphtyl)-N,N'-diphenylbenzidine (NPD) in 40 nm thickness, Blue Light-Emitting Material A in 20 nm thickness, and Compound shown in Table 1 in 40 nm thickness in this order under a condition of $1.0 \times 10^{-3}$ to $1.3 \times 10^{-3}$ Pa. Then, on the resulting laminate was disposed a mask patterned for a light-emitting area of 4 mm×5 mm, magnesium and silver (mole ratio: magnesium/silver=10/1) was co-vapor-deposited thereon into 250 nm, and silver was further vapor-deposited thereon into 300 nm under a condition of $1.0 \times 10^{-3}$ to $1.3 \times 10^{3}$ Pa, whereby the light-emitting devices 101 to 113 shown in Table 1 were produced, respectively. Incidentally, the light-emitting devices 101 to 113 were sealed in a dried glove box.

Thus-obtained each light-emitting device was made to emit light while applying direct current voltage thereto by "Source-Measure Unit 2400" manufactured by TOYO CORPORATION, and measured with respect to luminance, emission wavelength and chromaticity coordinates (CIE). The luminance was measured by "Luminance Meter BM-8" manufactured by TOPCON CORPORATION, and the emission wavelength and the chromaticity coordinates were measured by "Spectral Analyzer PMA-11" manufactured by Hamamatsu Photonics K.K. Further, each light-emitting device was allowed to stand at 85° C. under a condition of 70% RH for 3 days, and then, evaluated with respect to a relative luminance at a driving voltage of 10 V and the existence of a dark spot in the light-emitting surface. Incidentally, the relative liminance was a value relative to the standard value of 100, which expressed the luminance measured immediately after the production of the light-emitting device at a driving voltage of 10 V. The dark spot was a portion that emitted no light, and the existence of the dark spot was evaluated by visual observation. The results are shown in Table 1. Blue Light-Emitting Material A and Comparative Compounds 1 to 5 will be shown below.

TABLE 1

| Light-Emitting Device | Compound | Emission Wavelength $\lambda_{max}$ (nm) | Maximum Luminance (cd/m²) | Chromaticity Coordinates (X, Y) | Minimum Driving Voltage (V) | Relative Luminance | Dark Spot | |
|---|---|---|---|---|---|---|---|---|
| 101 | Comparative Compound 1 | 460 | 510 | (0.15, 0.15) | 6 | 79 | Not Observed | Comparative |
| 102 | Comparative Compound 2 | 462 | 320 | (0.15, 0.15) | 7 | 19 | Observed | Comparative |
| 103 | Comparative Compound 3 | 461 | 660 | (0.15, 0.15) | 6 | 12 | Observed | Comparative |
| 104 | Comparative Compound 4 | 460 | 710 | (0.15, 0.14) | 6 | 17 | Observed | Comparative |

TABLE 1-continued

| Light-Emitting Device | Compound | Emission Wavelength $\lambda_{max}$ (nm) | Maximum Luminance (cd/m²) | Chromaticity Coordinates (X, Y) | Minimum Driving Voltage (V) | Relative Luminance | Dark Spot | |
|---|---|---|---|---|---|---|---|---|
| 105 | (E-13) | 460 | 2711 | (0.15, 0.14) | 4 | 88 | Not Observed | Present Invention |
| 106 | (E-16) | 461 | 3030 | (0.15, 0.16) | 4 | 91 | Not Observed | Present Invention |
| 107 | (E-20) | 461 | 3798 | (0.15, 0.15) | 4 | 93 | Not Observed | Present Invention |
| 108 | (E-41) | 462 | 2560 | (0.15, 0.14) | 4 | 86 | Not Observed | Present Invention |
| 109 | (E-42) | 461 | 4013 | (0.15, 0.14) | 4 | 95 | Not Observed | Present Invention |
| 110 | (E-43) | 461 | 3489 | (0.15, 0.15) | 4 | 94 | Not Observed | Present Invention |
| 111 | (E-51) | 461 | 3120 | (0.15, 0.15) | 4 | 87 | Not Observed | Present Invention |
| 112 | (E-57) | 461 | 3830 | (0.15, 0.15) | 4 | 94 | Not Observed | Present Invention |
| 113 | Comparative Compound 5 | 461 | 240 | (0.15, 0.15) | 6 | 35 | Observed | Comparative |

Blue Light-Emitting Material A

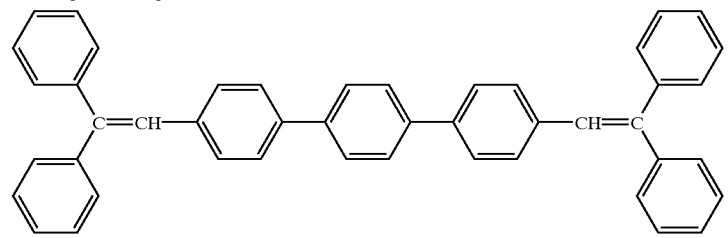

Comparative Compound 1 disclosed in Japanese Patent Laid-Open No. 10-92578

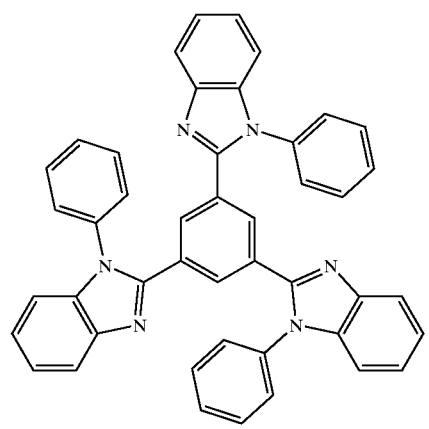

Comparative Compound 2 (PBD)

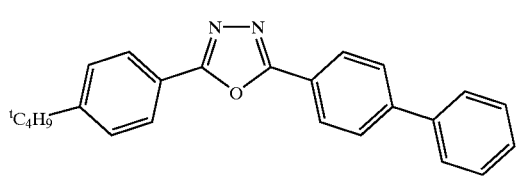

Comparative Compound 3 disclosed in Japanese Patent Laid-Open No. 2000-63818

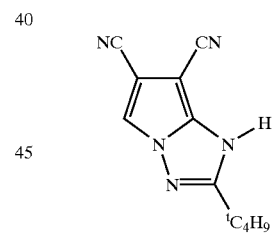

Comparative Compound 4

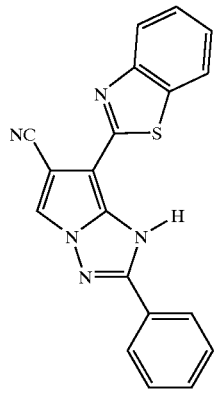

Comparative Compound 5

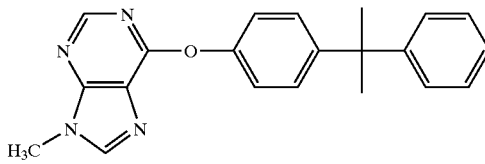

As shown in Table 1, the Compound (I) having a purine skeleton acted as an electron-transporting material in a non-doped type, light-emitting device, so that each of the light-emitting devices 105 to 112 according to the present invention using the Compound (I) emitted a blue light with high luminance and excellent color purity. Further, each of the light-emitting devices 105 to 112 according to the present invention was not extremely lowered in the luminance and provided no dark spot during the storage at a high temperature, to be excellent in durability.

Example 2

A glass substrate of 25 mm×25 mm×0.7 mm in size having an ITO positive electrode of 150 nm thickness, which was manufactured by Sanyo Vacuum Industries Co., Ltd., was subjected to etching and washing. On the ITO positive electrode was vapor-deposited copper phthalocyanine in approximately 10 nm thickness, and further, thereon were vacuum vapor-deposited N,N'-bis(3-methylphenyl)-N,N'-diphenylbenzidine (TPD) in approximately 40 nm thickness, a material composed of Host Material and Light-Emitting Material shown in Table 2 in approximately 20 nm thickness, bathocuproin in approximately 6 nm thickness and tris(8-hydroxyquinolinato)aluminum (Alq) in approximately 20 nm thickness in this order at the room temperature under a condition of $10^{-3}$ to $10^{-4}$ Pa. Then, on the resulting laminate was disposed a mask patterned for a light-emitting area of 5 mm×4 mm, magnesium and silver (mole ratio:magnesium/silver=10/1) was co-vapor-deposited thereon into 250 nm and silver was further vapor-deposited thereon into 300 nm in a deposition apparatus, whereby the light-emitting devices 201 to 221 shown in Table 2 were produced, respectively.

Thus-obtained each light-emitting device was made to emit light while applying direct current voltage by "Source-Measure Unit 2400" manufactured by TOYO CORPORATION, and measured with respect to luminance and emission wavelength. The luminance was measured by "Luminance Meter BM-8" manufactured by TOPCON CORPORATION, and the emission wavelength was measured by "Spectral Analyzer PMA-11" manufactured by Hamamatsu Photonics K.K. Further, each light-emitting device was put in an autoclave where the inner atmosphere was replaced with argon gas, allowed to stand at 85° C. for 3 days, and then, measured with respect to luminance and evaluated with respect to the existence of the dark spot in the light-emitting surface. The results are shown in Table 2, and structure of CBP will be shown below.

TABLE 2

| Light-Emitting Device | Host Material | Light-Emitting Material | Emission Wavelength $\lambda_{max}$ (nm) | |
|---|---|---|---|---|
| 201 | CBP | K-1 | 513 | Comparative |
| 202 | CBP | K-2 | 488 | Comparative |

TABLE 2-continued

| | | | | |
|---|---|---|---|---|
| 203 | CBP | K-30 | 468 | Comparative |
| 204 | (E-13) | K-1 | 514 | Present Invention |
| 205 | (E-13) | K-2 | 488 | Present Invention |
| 206 | (E-13) | K-30 | 469 | Present Invention |
| 207 | (E-16) | K-1 | 514 | Present Invention |
| 208 | (E-16) | K-2 | 487 | Present Invention |
| 209 | (E-43) | K-1 | 513 | Present Invention |
| 210 | (E-43) | K-2 | 488 | Present Invention |
| 211 | (E-43) | K-30 | 466 | Present Invention |
| 212 | (E-50) | K-1 | 512 | Present Invention |
| 213 | (E-50) | K-2 | 487 | Present Invention |
| 214 | (E-51) | K-1 | 514 | Present Invention |
| 215 | (E-51) | K-2 | 489 | Present Invention |
| 216 | (E-60) | K-1 | 513 | Present Invention |
| 217 | (E-60) | K-2 | 487 | Present Invention |
| 218 | (E-60) | K-30 | 468 | Present Invention |
| 219 | (E-66) | K-1 | 513 | Present Invention |
| 220 | (E-66) | K-2 | 487 | Present Invention |
| 221 | (E-66) | K-30 | 468 | Present Invention |

| | Light-Emitting Properties Immediately after of Light-Emitting Device | | Production Light-Emitting Properties after Storage at 85° C. | |
|---|---|---|---|---|
| Light-Emitting Device | Luminance (at Applying Voltage of 12 V, cd/m²) | External Quantum Efficiency (%) | Luminance (at Applying Voltage of 12 V, cd/m²) | Dark Spot |
| 201 | 36600 | 8.1 | 11700 | Observed |
| 202 | 8200 | 6.4 | 3000 | Observed |
| 203 | 4000 | 1.8 | 800 | Observed |
| 204 | 42100 | 9.9 | 38100 | Hardly Observed |
| 205 | 9200 | 7.3 | 7800 | Hardly Observed |
| 206 | 11000 | 5.3 | 9700 | Hardly Observed |
| 207 | 37800 | 9.3 | 30900 | Hardly Observed |
| 208 | 8800 | 7.1 | 7900 | Hardly Observed |
| 209 | 40400 | 8.8 | 37400 | Hardly Observed |
| 210 | 9100 | 6.8 | 8200 | Hardly Observed |
| 211 | 8900 | 4.6 | 8100 | Hardly Observed |
| 212 | 38800 | 9.7 | 33700 | Hardly Observed |
| 213 | 8900 | 7.8 | 7700 | Hardly Observed |
| 214 | 37000 | 8.6 | 34600 | Hardly Observed |
| 215 | 8700 | 7.2 | 7600 | Hardly Observed |
| 216 | 39600 | 10.5 | 32400 | Hardly Observed |
| 217 | 9700 | 8.5 | 8100 | Hardly Observed |
| 218 | 10600 | 6.4 | 8600 | Hardly Observed |
| 219 | 40800 | 11.4 | 33200 | Hardly Observed |
| 220 | 11200 | 9.2 | 9100 | Hardly Observed |
| 221 | 11000 | 7.3 | 8600 | Hardly Observed |

CBP disclosed in Applied Physics Letters, 75, 4 (1999)

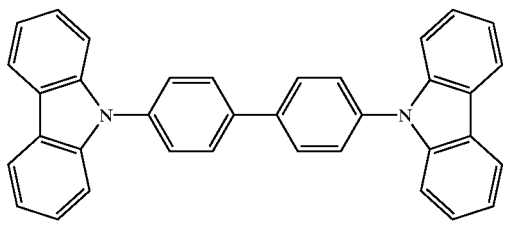

As shown in Table 2, the comparative light-emitting devices 201 to 203 using CBP as a host material exhibited remarkable reduction of the luminance and the presence of the dark spot after the storage at the high temperature. As compared with this, the light-emitting devices 204 to 221 according to the present invention using the Compound (I) having a purine skeleton exhibited only a little reduction of the luminance and an excellent light-emitting surface after the storage, to be improved in durability.

Example 3

A glass substrate of 25 mm×25 mm×0.7 mm in size having an ITO positive electrode of 150 nm thickness, which was manufactured by Sanyo Vacuum Industries Co., Ltd., was subjected to etching and washing. The ITO positive electrode was spin-coated with a solution prepared by dissolving 40 mg of poly(N-vinylcarbazole) (PVK), 12 mg of 2-(4-tert-butylphenyl)-5-(biphenyl -4-yl)-1,3,4-oxadiazole (PBD) and 1 mg of the light emitting material K-1 in 3 ml of 1,2-dichloroethane. The resultant organic layer disposed on the ITO positive electrode had thickness of approximately 120 nm. Then, a negative electrode was disposed on the organic layer by vapor deposition in the same manner as Example 2 to produce the light-emitting device 301 shown in Table 3. Further, light-emitting devices 302 to 319 were produced in the same manner as the light-emitting device 301 except for using 20 mg of Host Material and 1 mg of Light-Emitting Material shown in Table 3. Structures of PVK and PBD will be shown below.

PVK

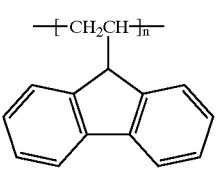

Weight-Average Molecular Weight
(determined by polystyrene standard): 23,000

PBD

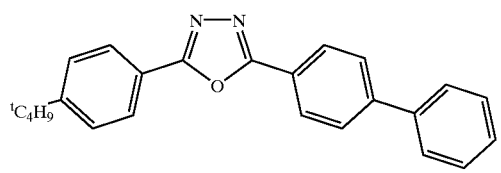

Coumarin 6

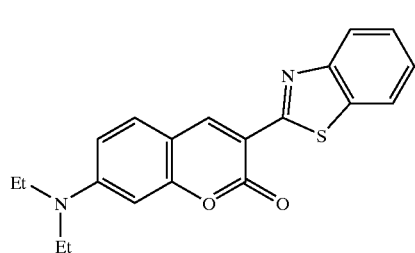

Thus-obtained each light-emitting device was made to emit light while applying direct current voltage by "Source-Measure Unit 2400" manufactured by TOYO CORPORATION, and measured with respect to luminance and emission wavelength. The luminance was measured by "Luminance Meter BM-8" manufactured by TOPCON CORPORATION, and the emission wavelength was measured by "Spectral Analyzer PMA-11" manufactured by Hamamatsu Photonics K.K. Further, each light-emitting device was put in an autoclave where the inner atmosphere was replaced with argon, allowed to stand at 85° C. for 3 days, and then, measured with respect to luminance and evaluated with respect to the existence of the dark spot in the light-emitting surface. The results are shown in Table 3.

TABLE 3

| Light-Emitting Device | Host Material | Light-Emitting Material | Emission Wavelength $\lambda_{max}$ (nm) | |
|---|---|---|---|---|
| 301 | — | K-1 | 514 | Comparative |
| 302 | — | K-2 | 488 | Comparative |
| 303 | CBP | K-1 | 513 | Comparative |
| 304 | CBP | K-2 | 488 | Comparative |
| 305 | (E-8) | K-1 | 513 | Present Invention |
| 306 | (E-20) | K-1 | 514 | Present Invention |
| 307 | (E-41) | K-1 | 513 | Present Invention |
| 308 | (E-42) | K-1 | 513 | Present Invention |
| 309 | (E-42) | K-2 | 487 | Present Invention |
| 310 | (E-43) | K-1 | 512 | Present Invention |
| 311 | (E-44) | K-1 | 513 | Present Invention |
| 312 | (E-45) | K-1 | 514 | Present Invention |
| 313 | (E-46) | K-1 | 513 | Present Invention |
| 314 | (E-51) | K-1 | 514 | Present Invention |
| 315 | (E-51) | K-2 | 488 | Present Invention |
| 316 | (E-52) | K-1 | 513 | Present Invention |
| 317 | (E-52) | K-2 | 487 | Present Invention |
| 318 | Comparative Compound 5 | K-1 | 514 | Comparative |
| 319 | Comparative Compound 5 | K-2 | 488 | Comparative |

| | Light-Emitting Properties Immediately after of Light-Emitting Device | | Production Light-Emitting Properties after Storage at 85° C. | |
|---|---|---|---|---|
| Light-Emitting Device | Luminance (at Applying Voltage of 18 V, cd/m$^2$) | External Quantum Efficiency (%) | Luminance (at Applying Voltage of 18 V, cd/m$^2$) | Dark Spot |
| 301 | 11200 | 2.6 | 3200 | Observed |
| 302 | 8400 | 2 | 2100 | Observed |
| 303 | 12300 | 2.9 | 2800 | Observed |
| 304 | 9600 | 2.3 | 1600 | Observed |
| 305 | 17600 | 4.1 | 13600 | Hardly Observed |
| 306 | 14800 | 3.6 | 11700 | Hardly Observed |
| 307 | 16700 | 3.7 | 12600 | Hardly Observed |
| 308 | 15200 | 3.6 | 11900 | Hardly Observed |
| 309 | 12900 | 3.1 | 9600 | Hardly Observed |
| 310 | 14300 | 3.6 | 11000 | Hardly Observed |
| 311 | 15000 | 3.7 | 11400 | Hardly Observed |
| 312 | 17200 | 3.8 | 13900 | Hardly Observed |
| 313 | 14600 | 3.6 | 11800 | Hardly Observed |
| 314 | 17700 | 3.5 | 12400 | Hardly Observed |
| 315 | 11900 | 3.8 | 10400 | Hardly Observed |
| 316 | 18200 | 3.8 | 14800 | Hardly Observed |
| 317 | 12800 | 4.2 | 12100 | Hardly Observed |
| 318 | 13400 | 3.2 | 5800 | Observed |
| 319 | 10600 | 2.7 | 4100 | Observed |

As shown in Table 3, although a coating type, light-emitting device was conventionally poor in the light-emitting efficiency in general, the light-emitting devices 305 to 317 according to the present invention using the Compound (I) having a purine skeleton were high in the luminance and the light-emitting efficiency and excellent in the durability.

Example 4

A glass substrate of 25 mm×25 mm×0.7 mm in size having an ITO positive electrode of 150 nm thickness, which was manufactured by Sanyo Vacuum Industries Co., Ltd., was subjected to etching and washing. On the ITO positive electrode were vacuum vapor-deposited tetrakis(4-diphenylaminophenyl)silane in approximately 50 nm thickness, a material composed of Host Material and Light-Emitting Material shown in Table 4 in approximately 36 nm thickness and Compound (17) in approximately 36 nm thickness in this order at the room temperature under a condition of $10^{-3}$ to $10^{-4}$ Pa. Then, on the resulting laminate was disposed a mask patterned for a light-emitting area of 5 mm×4 mm, magnesium and silver (mole ratio:magnesium/silver=10/1) was co-vapor-deposited thereon into 250 nm and silver was further vapor-deposited thereon into 300 nm in a deposition apparatus, whereby the light-emitting devices 401 to 407 shown in Table 4 were produced, respectively. Thus-obtained each light-emitting device was measured with respect to luminance and emission wavelength and evaluated with respect to the existence of the dark spot in the same manner as Example 2. The results are shown in Table 4, and structure of Compound (17) will be shown below.

the dark spot after the storage at the high temperature. As compared with this, the light-emitting devices 402 to 407 according to the present invention using the Compound (I) having a purine skeleton were high in the luminance and the external quantum efficiency immediately after production of light-emitting device, and exhibited only a little reduction of the luminance and an excellent light-emitting surface after the storage, to be excellent in both of the light-emitting properties and the durability.

As described in detail above, the light-emitting device of the present invention uses the compound of the formula (I) having a purine skeleton as the host material, the charge-transporting material, etc., to emit light with high luminance and excellent light-emitting efficiency. Further, the light-

TABLE 4

(17)

| Light-Emitting Device | Host Material | Light-Emitting Material | Emission Wavelength $\lambda_{max}$ (nm) | |
|---|---|---|---|---|
| 401 | CBP | K-50 | 485 | Comparative |
| 402 | (E-13) | K-50 | 463 | Present Invention |
| 403 | (E-42) | K-50 | 463 | Present invention |
| 404 | (E-47) | K-50 | 463 | Present Invention |
| 405 | (E-48) | K-50 | 463 | Present Invention |
| 406 | (E-51) | K-50 | 463 | Present Invention |
| 407 | (E-57) | K-50 | 463 | Present Invention |

| Light-Emitting Device | Light-Emitting Properties Immediately after Production of Light-Emitting Device | | Light-Emitting Properties after Storage at 85° C. | |
|---|---|---|---|---|
| | Luminance (at Applying Voltage of 12 V, cd/m²) | External Quantum Efficiency (%) | Luminance (at Applying Voltage of 12 V, cd/m²) | Dark Spot |
| 401 | 216 | 0.9 | 32 | Observed |
| 402 | 4400 | 7.2 | 3200 | Hardly Observed |
| 403 | 4100 | 6.6 | 3400 | Hardly Observed |
| 404 | 4700 | 7.5 | 3000 | Hardly Observed |
| 405 | 5200 | 8.1 | 4100 | Hardly Observed |
| 406 | 5400 | 8.7 | 4600 | Hardly Observed |
| 407 | 5600 | 10.0 | 4800 | Hardly Observed |

As shown in Table 4, the comparative light-emitting device 401 using CBP as a host material was low in the luminance and the external quantum efficiency immediately after production of light-emitting device, and exhibited remarkable reduction of the luminance and the presence of emitting device of the present invention exhibits only a little reduction of the luminance and has an excellent light-emitting surface after storage at a high temperature, to be excellent in durability. Although a conventional, coating type, light-emitting device has been poor in light-emitting efficiency, the coating type, light-emitting device according to the present invention is excellent in both of light-emitting properties and durability.

What is claimed is:

1. A light-emitting device comprising a pair of electrodes and one or more organic layers disposed between said electrodes, said one or more organic layers comprising a light-emitting layer, wherein at least one of said one or more organic layers comprises a compound represented by the following formula (IV):

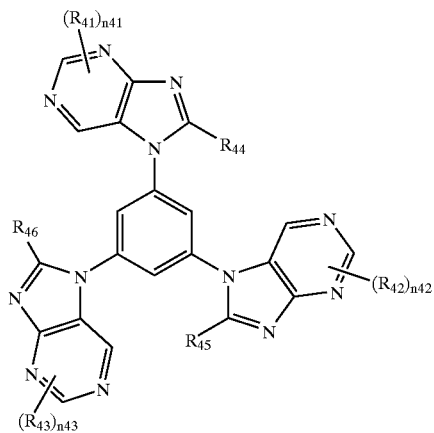

Formula (IV)

wherein $R_{41}$, $R_{42}$ and $R_{43}$ represent a substituent; $R_{44}$, $R_{45}$ and $R_{46}$ represent a hydrogen atom or a substituent; and n41, n42 and n43 represent an integer of 0 to 2.

2. A light-emitting device comprising a pair of electrodes and one or more organic layers disposed between said electrodes, said one or more organic layers comprising a light-emitting layer, wherein at least one of said one or more organic layers comprises a compound represented by the following formula (XII):

Formula (XII)

wherein $R_{121}$ and $R_{122}$ independently represent a substituent; $R_{123}$ and $R_{124}$ independently represent a hydrogen atom or a substituent; $R_{125}$ and $R_{126}$ independently represent a substituent; $n_{121}$ and $n_{122}$ independently represent an integer of 0 to 2; n125 and n126 independently represent an integer of 0 to 4; and $L_{121}$ represents a single bond or a linking group.

3. The light-emitting device of claim 1, wherein at least one of said one or more organic layers comprises said compound dispersed in a polymer.

4. The light-emitting device of claim 1, wherein a least one of said one or more organic layers comprises said compound and a transition metal complex.

5. The light-emitting device of claim 4, wherein said transition metal complex is an ortho-metallation complex.

6. The light-emitting device of claim 1, wherein said compound is used as a host material, a weight ratio of said compound being 1 to 99 weight % based on the total of the organic layer comprising said compound.

7. The light-emitting device of claim 1, wherein said compound is used as a material other than a host material, a weight ratio of said compound being 1 to 100 weight % based on the total of the organic layer comprising said compound.

8. A heterocyclic compound represented by formula (IV):

Formula (IV)

wherein $R_{41}$, $R_{42}$ and $R_{43}$ independently represent a substituent; $R_{44}$, $R_{45}$ and $R_{46}$ independently represent a hydrogen atom or a substituent; and n41, n42 and n43 independently represent an integer of 0 to 2.

9. A heterocyclic compound represented by formula (XII):

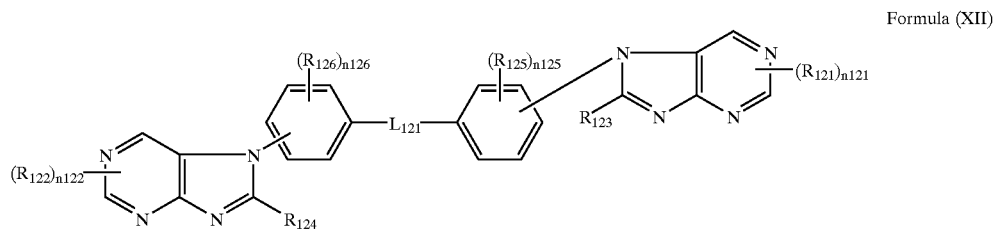

Formula (XII)

wherein $R_{121}$ and $R_{122}$ independently represent a substituent; $R_{123}$ and $R_{124}$ independently represent a hydrogen atom or a substituent; $R_{125}$ and $R_{126}$ independently represent a substituent; n121 and n122 independently represent an integer of 0 to 2; n125 and n126 independently represent an integer of 0 to 4; and $L_{121}$ represents a single bond or a linking group.

* * * * *